(12) United States Patent
Dumetz et al.

(10) Patent No.: US 11,530,238 B2
(45) Date of Patent: Dec. 20, 2022

(54) METHODS FOR PURIFYING ANTIBODIES

(71) Applicant: GlaxoSmithKline Intellectual Property Development Limited, Middlesex (GB)

(72) Inventors: Andre C. Dumetz, King of Prussia, PA (US); Kent E. Goklen, King of Prussia, PA (US); Nicholas E. Levy, King of Prussia, PA (US); Jessica Rachel Molek, King of Prussia, PA (US); Andrew S. Thomson, Collegeville, PA (US); Kenneth G. Yancey, Wayne, PA (US)

(73) Assignee: GLAXOSMITHKLINE INTELLECTUAL PROPERTY DEVELOPMENT LIMITED, Middlesex (GB)

( * ) Notice: Subject to any disclaimer, the term of this patent is extended or adjusted under 35 U.S.C. 154(b) by 820 days.

(21) Appl. No.: 16/330,588

(22) PCT Filed: Sep. 6, 2017

(86) PCT No.: PCT/IB2017/055374
§ 371 (c)(1),
(2) Date: Mar. 5, 2019

(87) PCT Pub. No.: WO2018/047080
PCT Pub. Date: Mar. 15, 2018

(65) Prior Publication Data
US 2021/0284686 A1   Sep. 16, 2021

Related U.S. Application Data

(60) Provisional application No. 62/384,240, filed on Sep. 7, 2016.

(51) Int. Cl.
| C07K 1/22 | (2006.01) |
| B01D 15/38 | (2006.01) |
| B01D 15/42 | (2006.01) |
| C07K 16/06 | (2006.01) |

(52) U.S. Cl.
CPC ............ *C07K 1/22* (2013.01); *B01D 15/3809* (2013.01); *B01D 15/424* (2013.01); *C07K 16/065* (2013.01)

(58) Field of Classification Search
None
See application file for complete search history.

(56) References Cited

U.S. PATENT DOCUMENTS

| 5,429,746 | A | 7/1995 | Shadle et al. |
| 10,676,503 | B2 * | 6/2020 | Goklen .............. B01D 15/3809 |
| 2003/0152966 | A1 | 8/2003 | Alred et al. |
| 2008/0167450 | A1 | 7/2008 | Pan |
| 2008/0182979 | A1 | 7/2008 | Lihme et al. |
| 2012/0122759 | A1 * | 5/2012 | Brown .................. C07K 16/065 530/344 |
| 2016/0108084 | A1 | 4/2016 | Gruber et al. |
| 2016/0319012 | A1 * | 11/2016 | Yu ............................ C07K 1/18 |

FOREIGN PATENT DOCUMENTS

| CN | 1922207 A | 2/2007 |
| JP | 2009-522580 A | 6/2009 |
| JP | 2010-502737 A | 1/2010 |
| JP | 2016-519145 A | 6/2016 |
| WO | 03102208 A2 | 12/2003 |
| WO | 2005082937 A2 | 9/2005 |
| WO | 2005113604 A2 | 12/2005 |
| WO | 2007081851 A2 | 7/2007 |
| WO | 2007109163 A2 | 9/2007 |
| WO | WO-2007117490 A2 * | 10/2007 ........... A61K 31/519 |
| WO | WO 2008/031020 A2 | 3/2008 |
| WO | 2012135415 A1 | 10/2012 |
| WO | WO 2014/141150 A1 | 9/2014 |
| WO | WO 2014/186350 A1 | 11/2014 |
| WO | 2015/038888 A1 | 3/2015 |
| WO | 2015038888 A1 | 3/2015 |

OTHER PUBLICATIONS

Chollangi, S. et al. "Development of Robust Antibody Purification by Optimizing Protein-A Chromatography in Combination with Precipitation Methodologies". Biotechnology and Bioengineering, 112(11): 2292-2304 (2015).

Aboulaich et al., "A Novel Approach to Monitor Clearance of Host Cell Proteins Associated with Monoclonal Antibodies", *Biotechnology Progress*, vol. 30, No. 5, pp. 1114-1124 (2014).

Levy et al., "Development and characterization of a protein A capture step for improved impurity clearance", Process Development, Biopharmaceutical Development, King of Prussia, PA, Washes—ACS BIOT Poster, Denver, 2015, 1 page.

Brodsky, Yan, et al., "Caprylic acid precipitation method for impurity reduction: an alternative to conventional chromatography for monoclonal antibody purification", Biotechnology and Bioengineering, vol. 109, No. 10, Oct. 2012, pp. 2589-2598.

Chhatre et al., "Evaluation of a novel agarose-based synthetic ligand adsorbent for the recovery of antibodies from ovine serum", J. Chromatogr. B Analyt. Technol. Biomed. Life Sci., 2007, vol. 860, No. 2, pp. 209-217.

(Continued)

*Primary Examiner* — Daniel E Kolker
*Assistant Examiner* — James L Rogers
(74) *Attorney, Agent, or Firm* — Taewoo Cho; Nicole Ginanni

(57) ABSTRACT

The present invention relates to a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising caprylate and arginine; and (c) eluting the recombinant polypeptide from the superantigen chromatography solid support.

17 Claims, 13 Drawing Sheets

(56) References Cited

OTHER PUBLICATIONS

Chollangi, S. et al., "Development of Robust Antibody Purification by Optimizing Protein-A Chromatography in Combination With Precipitated Methodologies", Biotechnology and Bioengineering (2015), vol. 112, No. 11, pp. 2292-2304.

Monie, Elin "Evaluation of the 96-well format for screening of chromatographic buffer conditions" Master's degree project, 58 pages, 2006.

Newcombe et al. "Optimised affinity purification of polyclonal antibodies from hyper immunised ovine serum using a synthetic Protein A adsorbent, MAbsorbent A2P", J. of Chromatography B, vol. 814, pp. 209-215, 2005.

Nilson, B. H. K., et al., "Purification of antibodies using protein L-binding framework structures in the light chain variable domain", Journal of Immunological Methods, vol. 164, No. 1, Aug. 26, 1993, pp. 33-40.

Tong, Hong-Fei, et al., "Caprylate as the albumin-selective modifier to improve IgG purification with hydrophobic charge-induction chromatography", Journal of Chromatography, A Apr. 12, 2013, vol. 1285, Feb. 15, 2013, pp. 88-96.

Li, Heping, "The Production Principle and Technology of Fine Chemicals", Henan Science and Technology Press, p. 336, Sep. 30, 1994, 4 pages (C1).

"Clinical Medical Examination", Fuzhou Army General Hospital, Shanghai Science and Technology Press, p. 253, Apr. 30, 1978, 7 pages (C2).

\* cited by examiner

METHODS FOR PURIFYING ANTIBODIES

This application is a § 371 of International Application No. PCT/IB2017/055374, filed Sep. 6, 2017, which claims the benefit of U.S. Provisional Application No. 62/384,240, filed Sep. 7, 2016.

FIELD OF THE INVENTION

The present invention relates to the field of protein purification using a superantigen such as Protein A, Protein G, or Protein L immobilized to a solid support. In particular, the invention relates to wash buffer components and methods of using the wash buffers to remove host cell impurities during wash steps, minimizing loss of the desired protein product.

BACKGROUND OF THE INVENTION

Host cell protein (HCP) impurities—classified by the FDA as "process-related" impurities—must be removed to sufficiently low levels in biopharmaceutical downstream processing. Adequate clearance of HCPs can be particularly challenging for some monoclonal antibody (mAb) products during typical downstream processing. The majority of mAb downstream processes utilize a 'platform' approach; the typical mAb downstream platform consists of protein A affinity chromatography capture, followed by one to three non-affinity polishing steps. The protein A affinity capture step is the workhorse of the platform and provides the large majority of HCP clearance. The subsequent polishing steps are generally ion-exchange, hydrophobic interaction or multimodal chromatography.

For many mAb products the HCP concentration is sufficiently low after the first polishing chromatography step. However, there are many mAbs for which a second polishing chromatography step is implemented specifically to remove additional HCPs; this can require significant process development effort and results in greater process complexity. Previous studies have identified a sub-population of HCP impurities that have an attractive interaction with the mAb product molecule (Levy et al., (2014) Biotechnol. Bioeng. 111(5):904-912; Aboulaich et al., (2014) Biotechnol. Prog. 30(5):1114-1124). The majority of HCPs that evade clearance through the protein A step are due to product-association rather than co-elution or adsorption to the protein A ligand or base matrix. The population of difficult-to-remove HCPs is relatively small—compared to the diverse population of HCPs present in cell culture—and similar for different mAb products.

Although the population of difficult HCP impurities is largely identical for all mAb products, varying degrees of HCP-mAb interactions can significantly impact the total HCP clearance across the protein A step; very minor changes to the amino acid sequence of mAb products can impact HCP-mAb interactions in the protein A and polishing steps. The population of HCPs loaded onto the protein A column, which has an obvious impact on the potential for HCP-mAb association, can be affected by cell age, harvest methodology and conditions, and small differences have been observed between different host cell lines. In addition to product-association, for most protein A resins there is a low level of HCP impurities that bind to the base matrix and co-elute with the product. Controlled pore glass resins have much higher levels of HCP bound to the base matrix.

One particular wash additive, sodium caprylate, has previously been identified as one of the most successful for disrupting HCP-mAb associations and resulting in low HCP concentrations in the protein A eluate. Sodium caprylate (also known as sodium octanoate) is an eight-carbon saturated fatty acid found to be non-toxic in mice with a critical micelle concentration of approximately 360 mM. Previous studies have used 50 mM sodium caprylate (Aboulaich et al., (2014) Biotechnol. Prog. 30(5):1114-1124), 40 mM sodium caprylate with varying NaCl and pH (Chollangi et al., (2015) Biotechnol. Bioeng. 112(11):2292-2304), and up to 80 mM sodium caprylate (Herzer et al., (2015) Biotechnol. Bioeng. 112(7):1417-1428), for improving HCP clearance, and 50 mM sodium caprylate at high pH with NaCl for both total HCP clearance and removal of a proteolytic HCP impurity (Bee et al., (2015) Biotechnol. Prog. 31(5):1360-1369). Patent applications have previously been filed for protein A washes containing up to 100 mM sodium caprylate (WO2014/141150; WO2014/186350). Additionally, caprylic acid has been used for precipitation of host cell protein impurities in non-chromatographic processes before and after the Protein A capture step (Brodsky et al., (2012) Biotechnol. Bioeng. 109(10): 2589-2598; Zheng et al., (2015) Biotechnol. Prog. 31(6):1515-1525; Herzer et al., (2015) Biotechnol. Bioeng. 112(7):1417-1428).

There is a need in the art to provide improved methods of purifying proteins, in particular antibodies, from host cell proteins.

SUMMARY OF THE INVENTION

The present invention provides a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising greater than about 50 mM caprylate and greater than about 0.5 M arginine; and (c) eluting the recombinant polypeptide from the superantigen chromatography solid support.

In another embodiment, the caprylate is sodium caprylate. In yet another embodiment, the wash buffer comprises about 75 mM to about 300 mM caprylate.

In another aspect of the invention, the wash buffer comprises about 0.75 M to about 1.5 M arginine.

In another aspect of the invention, the wash buffer further comprises about 0.5 M to about 1 M lysine.

In one embodiment of the invention, the eluted recombinant polypeptide contains less than about 2% fragmented recombinant polypeptide.

In one aspect of the invention, the HCP is derived from a mammalian cell, for example, the HCP is phospholipase B-Like 2 protein and/or cathepsin L. In yet another aspect of the invention, the purification of the recombinant polypeptide from cathepsin L is measured by a reduced cathepsin L activity in the eluate of step (c).

In one embodiment, the pH of the wash buffer is between pH 7 to pH 9; or pH 7.5 to pH 8.5.

In another embodiment of the invention, the recombinant polypeptide is a monoclonal antibody (mAb), such as, for example, an IgG1, or an IgG4.

In yet another embodiment, the wash buffer does not contain sodium chloride.

In one aspect of the invention, the superantigen is selected from the group consisting of Protein A, Protein G, and Protein L.

In another aspect of the invention, after step (c) the amount of HCP is less than about 200 ng HCP/mg product.

The present invention provides a method of purifying a recombinant polypeptide from Host Cell Proteins (HCP), the method comprising: (a) applying a solution comprising the recombinant polypeptide and HCP to a superantigen chromatography solid support; (b1) washing the superantigen chromatography solid support with a wash buffer comprising greater than about 50 mM caprylate; (b2) washing the superantigen chromatography solid support with a wash buffer comprising greater than about 0.5 M arginine; and (c) eluting the recombinant polypeptide from the superantigen chromatography solid support.

The present invention also provides a method of purifying a recombinant polypeptide from Host Cell Proteins (HCP), the method comprising: (a) applying a solution comprising the recombinant polypeptide and HCP to a superantigen chromatography solid support; (b1) washing the superantigen chromatography solid support with a wash buffer comprising greater than about 0.5 M arginine arginine; (b2) washing the superantigen chromatography solid support with a wash buffer comprising greater than about 50 mM caprylate; and (c) eluting the recombinant polypeptide from the superantigen chromatography solid support.

In another embodiment, the invention provides a method of purifying a recombinant polypeptide from phospholipase B-Like 2 protein, the method comprising: (a) applying a solution comprising the recombinant polypeptide and HCP to a superantigen chromatography solid support, (b) washing the superantigen chromatography solid support with a wash buffer comprising about 100 mM caprylate and about 1.1 M arginine; and (c) eluting the recombinant polypeptide from the superantigen chromatography solid support.

In yet another embodiment, the invention provides method of purifying a recombinant polypeptide from cathepsin L, the method comprising: (a) applying a solution comprising the recombinant polypeptide and HCP to a superantigen chromatography solid support, (b) washing the superantigen chromatography solid support with a wash buffer comprising about 150 mM caprylate and about 1.1 M arginine; and (c) eluting the recombinant polypeptide from the superantigen chromatography solid support.

In one aspect, the invention provides a method of purifying a recombinant polypeptide from Host Cell Proteins (HCP), the method comprising: (a) applying a solution comprising the recombinant polypeptide and HCP to a superantigen chromatography solid support; (b) washing the superantigen chromatography solid support with a wash buffer comprising caprylate at a concentration greater than about 250 mM; and (c) eluting the recombinant polypeptide from the superantigen chromatography solid support.

In another aspect, the invention provides a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising about 150 mM to about 850 mM caprylate; and (c) eluting the recombinant polypeptide from the superantigen chromatography solid support.

In yet another aspect, the present invention provides a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising about 100 mM to about 850 mM caprylate and about 0.25 M to about 1.5 M arginine; and (c) eluting the recombinant polypeptide from the superantigen chromatography solid support.

DETAILED DESCRIPTION

Figure 1:
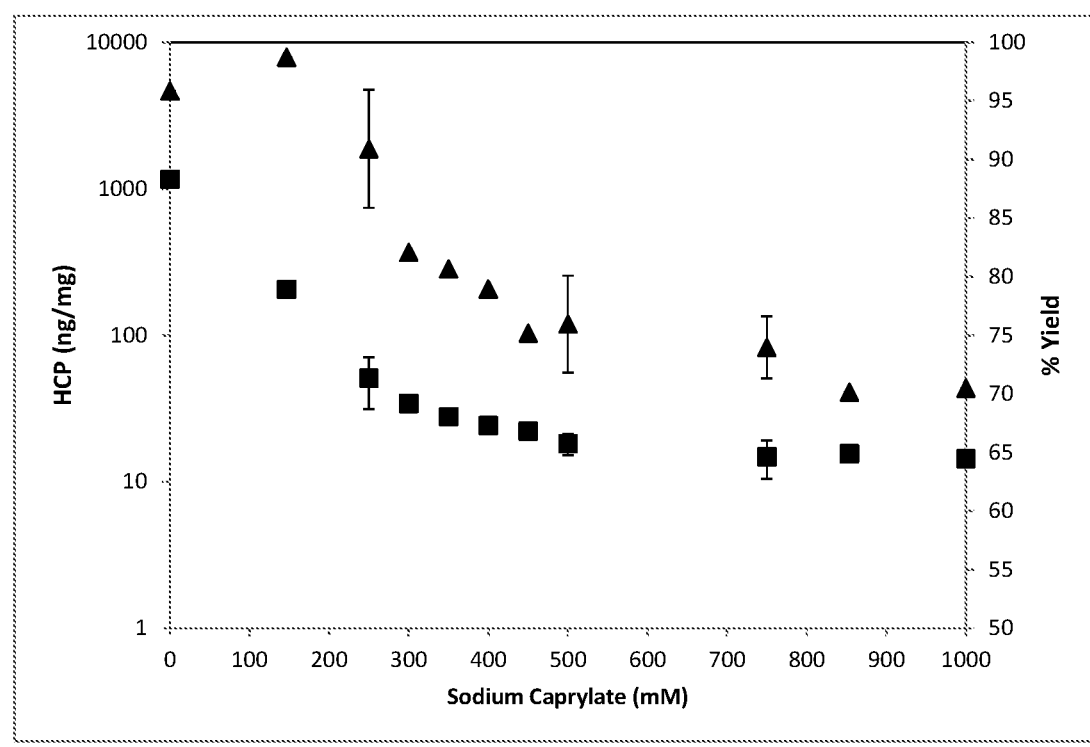
FIG. 1: Percent yield (triangles, ▲) and HCP concentration (squares, ■) in protein A eluate using mAb1 as a model with varying concentrations of sodium caprylate in the wash.

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a polypeptide" includes a combination of two or more polypeptides, and the like.

The term "comprising" encompasses "including" or "consisting" e.g. a composition "comprising" X may consist exclusively of X or may include something additional e.g. X+Y. The term "consisting essentially of" limits the scope of the feature to the specified materials or steps and those that do not materially affect the basic characteristic(s) of the claimed feature. The term "consisting of" excludes the presence of any additional component(s).

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine; D-p-fluorophenylalanine; D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine.

"Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the proteins described herein.

"Cationic" as used herein refers to any peptide that possesses a net positive charge at pH 7.4. The biological activity of the peptides can be determined by standard methods known to those of skill in the art and described herein.

"Recombinant" when used with reference to a protein indicates that the protein has been modified by the introduction of a heterologous nucleic acid or protein or the alteration of a native nucleic acid or protein.

As used herein a "therapeutic protein" refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

All "amino acid" residues identified herein are in the natural L-configuration. In keeping with standard polypeptide nomenclature, abbreviations for amino acid residues are as shown in the following table.

TABLE 1

Amino acid abbreviations.

| 1 Letter | 3 Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Purification Methods

In one aspect the present invention is directed to a method of purifying a recombinant polypeptide from Host Cell Proteins (HCP), the method comprising: (a) applying a solution comprising the recombinant polypeptide and HCP to a superantigen chromatography solid support; (b) washing the superantigen chromatography solid support with a wash buffer comprising caprylate and arginine; and (c) eluting the recombinant polypeptide from the superantigen chromatography solid support.

In one aspect the present invention is directed to a method of purifying a recombinant polypeptide from Host Cell Proteins (HCP), the method comprising: (a) applying a solution comprising the recombinant polypeptide and HCP to a superantigen chromatography solid support; (b) washing the superantigen chromatography solid support with a wash buffer comprising greater than about 50 mM caprylate and greater than about 0.5 M arginine; and (c) eluting the recombinant polypeptide from the superantigen chromatography solid support.

In one aspect the present invention is directed to a method of purifying a recombinant polypeptide from Host Cell Proteins (HCP), the method comprising: (a) applying a solution comprising the recombinant polypeptide and HCP to a superantigen chromatography solid support; (b) washing the superantigen chromatography solid support with a wash buffer comprising caprylate at a concentration greater than 250 mM; and (c) eluting the recombinant polypeptide from the superantigen chromatography solid support.

In one aspect the present invention is directed to a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising about 150 mM to about 850 mM caprylate; and (c) eluting the recombinant polypeptide from the superantigen chromatography solid support.

In another aspect the present invention is directed to a method of purifying a recombinant polypeptide from Host Cell Proteins (HCP), the method comprising: (a) applying a solution comprising the recombinant polypeptide and HCP to a superantigen chromatography solid support; (b1) washing the superantigen chromatography solid support with a first wash buffer comprising caprylate; (b2) washing the superantigen chromatography solid support with a second wash buffer comprising arginine; and (c) eluting the recombinant polypeptide from the superantigen chromatography solid support.

In another aspect the present invention is directed to a method of purifying a recombinant polypeptide from Host Cell Proteins (HCP), the method comprising: (a) applying a solution comprising the recombinant polypeptide and HCP to a superantigen chromatography solid support; (b1) washing the superantigen chromatography solid support with a first wash buffer comprising arginine; (b2) washing the superantigen chromatography solid support with a second wash buffer comprising caprylate; and (c) eluting the recombinant polypeptide from the superantigen chromatography solid support.

After applying (or loading) the solution to the superantigen chromatography solid support in step (a), the recombinant polypeptide will be adsorbed to the superantigen immobilized on the solid support. The HCP impurities can then be removed by contacting the immobilized superantigen containing the adsorbed recombinant polypeptide with a wash buffer as described herein.

"Superantigen" refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include, but are not limited to, Protein G, which binds the IgG constant region (Bjorck and Kronvall (1984) *J. Immunol.*, 133:969); Protein A which binds the IgG constant region and VH domains (Forsgren and Sjoquist, (1966) *J. Immunol.*, 97:822); and Protein L which binds VL domains (Bjorck, (1988) *J. Immunol.*, 140:1194). Therefore, in one embodiment the superantigen is selected from the group consisting of Protein A, Protein G, and Protein L.

When used herein, the term "Protein A" encompasses Protein A recovered from a native source thereof (e.g., the cell wall of *Staphylococcus aureus*), Protein A produced synthetically (e.g. by peptide synthesis or by recombinant techniques), and variants thereof which retain the ability to bind proteins which have a $C_H2/C_H3$ region. Protein A can be purchased commercially, for example from Repligen or Pharmacia.

As used herein, "affinity chromatography" is a chromatographic method that makes use of the specific, reversible interactions between biomolecules rather than general properties of the biomolecule such as isoelectric point, hydrophobicity, or size, to effect chromatographic separation. "Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains $C_H2$ and $C_H3$ or immunoglobulin domains substantially similar to these. In practice, Protein A chromatography involves using Protein A immobilized to a solid support. See Gagnon, Protein A Affinity Chromatography, Purification Tools for Monoclonal Antibodies, pp. 155-198, Validated Biosystems, (1996). Protein G and Protein L may also be used for affinity chromatography. The solid support is a non-aqueous matrix onto which Protein A adheres (for example, a column, resin, matrix, bead, gel, etc). Such supports include agarose, sepharose, glass, silica, polystyrene, collodion charcoal, sand, polymethacrylate, cross-linked poly(styrene-divinylbenzene), and agarose with dextran surface extender and any other suitable material. Such materials are well known in the art. Any suitable method can be used to affix the superantigen to the solid support. Methods for affixing proteins to suitable solid supports are well known in the art. See e.g. Ostrove, in Guide to Protein Purification, Methods in Enzymology, (1990) 182: 357-371. Such solid supports, with and without immobilized Protein A or Protein L, are readily available from many commercial sources such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden) and Millipore (Billerica, Mass.).

The method described herein may comprise one or more further purification steps, such as one or more further chromatography steps. In one embodiment, the one or more further chromatography steps are selected from the group consisting of: anion exchange chromatography, cation exchange chromatography and mixed-mode chromatography, in particular anion exchange chromatography.

In one embodiment, the method additionally comprises filtering the eluate produced by step (c) of the methods described herein.

In one embodiment the method further comprises the following steps after step (c): (d) titrating the solution containing the recovered protein to about pH 3.5 with 30 mM acetic acid, 100 mM HCl; (e) allowing the solution of step (d) to remain at about pH 3.5 for about 30 to about 60 minutes; and (f) adjusting the pH of the solution of step (e)

to about pH 7.5 with 1 M Tris. In one embodiment the method further comprises filtering the solution produced by step (f).

In one embodiment, the amount of recombinant protein applied to the column in step (a) (i.e. the load ratio) is 35 mg/ml or less, such as 30 mg/ml or less, 20 mg/ml or less, 15 mg/ml or less or 10 mg/ml or less. It will be understood that "load ratio" refers to milligrams (mg) of protein (e.g. monoclonal antibody) per millilitre (ml) of resin.

Wash Buffers

A "buffer" is a buffered solution that resists changes in pH by the action of its acid-base conjugate components. An "equilibration buffer" refers to a solution used to prepare the solid phase for chromatography. A "loading buffer" refers to a solution used to load the mixture of the protein and impurities onto the solid phase (i.e. chromatography matrix). The equilibration and loading buffers can be the same. A "wash buffer" refers to a solution used to remove remaining impurities from the solid phase after loading is completed. The "elution buffer" is used to remove the target protein from the chromatography matrix.

A "salt" is a compound formed by the interaction of an acid and a base.

In one aspect of the invention, the wash buffer comprises an aliphatic carboxylate. The aliphatic carboxylate can be either straight chained or branched. In certain embodiments the aliphatic carboxylate is an aliphatic carboxylic acid or salt thereof, or the source of the aliphatic carboxylate is an aliphatic carboxylic acid or salt thereof. In certain embodiments, the aliphatic carboxylate is straight chained and selected from the group consisting of methanoic (formic) acid, ethanoic (acetic) acid, propanoic (propionic) acid, butanoic (butyric) acid, pentanoic (valeric) acid, hexanoic (caproic) acid, heptanoic (enanthic) acid, octanoic (caprylic) acid, nonanoic (pelargonic) acid, decanoic (capric) acid, undecanoic (undecylic) acid, dodecanoic (lauric) acid, tridecanoic (tridecylic) acid, tetradecanoic (myristic) acid, pentadecanoic acid, hexadecanoic (palmitic) acid, heptadecanoic (margaric) acid, octadecanoic (stearic) acid, and icosanoic (arachididic) acid or any salts thereof. Accordingly, the aliphatic carboxylate can comprise a carbon backbone of 1-20 carbons in length. In one embodiment the aliphatic carboxylate comprises a 6-12 carbon backbone. In one embodiment the aliphatic carboxylate is selected from the group consisting of caproate, heptanoate, caprylate, decanoate, and dodecanoate. In a further embodiment, the aliphatic carboxylate is caprylate.

In one embodiment the source of the aliphatic carboxylate is selected from the group consisting of an aliphatic carboxylic acid, a sodium salt of an aliphatic carboxylic acid, a potassium salt of an aliphatic carboxylic acid, and an ammonium salt of an aliphatic carboxylic acid. In one embodiment the source of the aliphatic carboxylate is a sodium salt of an aliphatic carboxylic acid. In a further embodiment the wash buffer comprises sodium caprylate, sodium decanoate, or sodium dodecanoate, in particular sodium caprylate.

In one embodiment the wash buffer comprises greater than about 50 mM caprylate. In one embodiment the wash buffer comprises greater than about 200 mM caprylate. In one embodiment the wash buffer comprises greater than about 250 mM caprylate. In a further embodiment the wash buffer comprises at least about 50 mM caprylate, such as at least about 75 mM, about 100 mM, about 150 mM, about 200 mM, about 250 mM or about 300 mM caprylate. In one embodiment the wash buffer comprises less than about 850 mM caprylate, such as less than about 800 mM, about 750 mM, about 700 mM, about 650 mM, about 600 mM, about 550 mM, about 500 mM, about 450 mM, about 400 mM, about 350 mM, about 300 mM caprylate. In another embodiment, the wash buffer comprises about 100 mM, about 125 mM, about 150 mM, about 175 mM, about 200 mM, or about 250 mM caprylate.

In one embodiment the wash buffer comprises greater than about 50 mM sodium caprylate. In one embodiment the wash buffer comprises greater than about 200 mM sodium caprylate. In one embodiment the wash buffer comprises greater than about 250 mM sodium caprylate. In a further embodiment the wash buffer comprises at least about 50 mM sodium caprylate, such as at least about 75 mM, about 100 mM, about 150 mM, about 200 mM, about 250 mM or about 300 mM sodium caprylate. In one embodiment the wash buffer comprises less than about 850 mM sodium caprylate, such as less than about 800 mM, about 750 mM, about 700 mM, about 650 mM, about 600 mM, about 550 mM, about 500 mM, about 450 mM, about 400 mM, about 350 mM, about 300 mM sodium caprylate. In another embodiment, the wash buffer comprises about 100 mM, about 125 mM, about 150 mM, about 175 mM, about 200 mM, or about 250 mM sodium caprylate.

In one embodiment the wash buffer comprises about 50 mM to about 750 mM caprylate; about 50 mM to about 500 mM caprylate; about 75 mM to about 400 mM caprylate; about 75 mM to about 350 mM caprylate; about 75 mM to about 300 mM caprylate; about 75 mM to about 200 mM caprylate; greater than about 250 mM to about 750 mM caprylate; greater than about 250 mM to about 500 mM caprylate; greater than about 250 mM to about 400 mM caprylate; greater than about 250 mM to about 350 mM caprylate; or greater than about 250 mM to about 300 mM caprylate.

In one embodiment the wash buffer comprises about 50 mM to about 750 mM sodium caprylate; about 50 mM to about 500 mM sodium caprylate; about 75 mM to about 400 mM sodium caprylate; about 75 mM to about 350 mM sodium caprylate; about 75 mM to about 300 mM sodium caprylate; about 75 mM to about 200 mM sodium caprylate; greater than about 250 mM to about 750 mM sodium caprylate; greater than about 250 mM to about 500 mM sodium caprylate; greater than about 250 mM to about 400 mM sodium caprylate; greater than about 250 mM to about 350 mM sodium caprylate; or greater than about 250 mM to about 300 mM sodium caprylate.

In one embodiment the wash buffer comprises an organic acid, an alkaline metal or ammonium salt of the conjugate base of the organic acid, and an organic base. In one embodiment the wash buffer is made without the addition of NaCl.

In one embodiment, the conjugate base of the organic acid is the sodium, potassium, or ammonium salt of the conjugate base of the organic acid. In one embodiment, the organic acid is acetic acid and the conjugate base of acetic acid is the sodium salt (i.e. sodium acetate).

In one embodiment the wash buffer additionally comprises about 1 mM to about 500 mM acetic acid. In one embodiment the wash buffer comprises about 45 mM acetic acid. In one embodiment the wash buffer additionally comprises about 1 mM to about 500 mM Tris base. In one embodiment the wash buffer comprises about 55 mM Tris base. In one embodiment the wash buffer additionally comprises about 1 mM to about 500 mM sodium acetate. In one embodiment the wash buffer comprises about 300 mM sodium acetate.

In one embodiment, the pH of the wash buffer is between about pH 7 to about pH 9; for example from about pH 7.5 to about pH 8.5.

In one embodiment, the wash buffer comprises about 0.25 M to about 1.5 M arginine. In a further embodiment, the wash buffer comprises about 0.25 M to about 2 M arginine. In a further embodiment, the wash buffer comprises about 0.5 M to about 2 M arginine. In yet another embodiment, the wash buffer comprises about 0.75 M to about 1.5 M arginine. In a further embodiment, the wash buffer comprises about 1 M, about 1.1 M, about 1.2 M, about 1.3 M, about 1.4 M, about 1.5 M, about 1.6 M, about 1.7 M, about 1.8 M, about 1.9 M, or about 2 M arginine. In one embodiment, the wash buffer comprises about 0.5 M to about 2 M arginine, in particular about 0.75 M to about 2 M arginine. In a further embodiment, the wash buffer comprises greater than about 1 M arginine.

It will be understood that references to "arginine" not only refer to the natural amino acids, but also encompass arginine derivatives or salts thereof, such as arginine HCl, acetyl arginine, agmatine, arginic acid, N-alpha-butyroyl-L-arginine, or N-alpha-pyvaloyl arginine.

Alternatively, arginine could be included in the initial wash buffer (i.e. used simultaneously). Therefore, in one aspect the invention provides a method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising about 100 mM to about 850 mM caprylate and about 0.25 M to about 1.5 M arginine; and (c) eluting the recombinant polypeptide from the superantigen chromatography solid support. As shown in the Examples described herein, superantigen chromatography washes comprising a combination of caprylate and arginine had an unexpected synergistic effect of improved host cell protein clearance, in particular for removing PLBL2 and cathepsin L which are two particularly difficult host cell proteins to remove.

In one embodiment, the wash buffer comprises about 100 mM to about 750 mM caprylate; about 100 mM to about 500 mM caprylate; about 100 mM to about 400 mM caprylate; about 100 mM to about 350 mM caprylate; or about 100 mM to about 300 mM caprylate; and/or about 0.25 M to about 2 M arginine, about 0.5 M to about 1.5 M arginine; or about 0.5 M to about 1 M arginine.

In one embodiment, the wash buffer comprises about 100 mM to about 750 mM sodium caprylate; about 100 mM to about 500 mM sodium caprylate; about 100 mM to about 400 mM sodium caprylate; about 100 mM to about 350 mM sodium caprylate; or about 100 mM to about 300 mM sodium caprylate; and/or about 0.25 M to about 2 M arginine; about 0.5 M to about 1.5 M arginine; or about 0.5 M to about 1 M arginine.

In one embodiment, the wash buffer comprises about 0.5 M to about 2 M arginine and about 50 mM to about 750 mM sodium caprylate; about 0.5 M to about 1.5 M arginine and about 50 mM to about 500 mM sodium caprylate; or about 0.5 M to about 1.5 M arginine and about 50 mM to about 250 mM sodium caprylate.

In one embodiment, the wash buffer further comprises about 0.5 M to about 1 M lysine, such as about 0.75 M lysine. In this embodiment, the lysine is included in the initial wash buffer (i.e. used simultaneously). In an alternative embodiment, the lysine is included in a separate wash buffer (i.e. used sequentially). As shown in the Examples provided herein, the addition of lysine was shown to successfully reduce the elution volume.

Recombinant Polypeptides

In one embodiment the polypeptide is an antigen binding polypeptide. In one embodiment the antigen binding polypeptide is selected from the group consisting of an antibody, antibody fragment, immunoglobulin single variable domain (dAb), mAbdAb, Fab, F(ab')$_2$, Fv, disulphide linked Fv, scFv, closed conformation multispecific antibody, disulphide-linked scFv, diabody or a soluble receptor. In a further embodiment the antigen binding protein is an antibody, for example a monoclonal antibody (mAb). The terms, recombinant polypeptide, product molecule and mAb are used herein interchangeably. The antibody may be, for example, a chimeric, humanized or domain antibody.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., (1989) *Proc. Natl. Acad. Sci. USA*, 86:10029-10032, Hodgson et al., (1991) *Bio/Technology*, 9:421). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see for example EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U. S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person (see for example Chothia et al., (1989) Nature 342:877-883).

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH dAbs (nanobodies). Camelid VHH are immunoglobulin single variable domain polypeptides that are derived from species including camel, llama, alpaca, dromedary, and guanaco, which produce heavy chain antibodies naturally devoid of light chains. Such VHH domains may be humanized according to standard techniques available in the art, and such domains are still considered to be "domain antibodies" according to the invention. As used herein "VH includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. (2006) 44, 656-665 and US2005/0043519.

The terms "mAbdAb" and dAbmAb" are used herein to refer to antigen-binding proteins comprising a monoclonal antibody and at least one single domain antibody. The two terms can be used interchangeably, and are intended to have the same meaning as used herein.

Often, purification of recombinant polypeptides from host cell proteins results in fragmentation of the recombinant polypeptide. Applicants have discovered that when the purification methods described herein are utilized, the amount of recombinant polypeptide fragmentation is significantly reduced. In one embodiment, the eluted recombinant polypeptide contains less than about 10%, about 9%, about 8%, about 7%, about 6%, about 5%, about 4%, about 3%, about 2%, or about 1% fragmented recombinant polypeptide. In another embodiment, the recombinant polypeptide is an antibody and the eluted antibody contains less than about 10%, about 9%, about 8%, about 7%, about 6%, about 5%, about 4%, about 3%, about 2%, or about 1% fragmented antibody.

Host Cell Proteins

"Impurity" refers to any foreign or undesirable molecule that is present in the load sample prior to superantigen chromatography or following superantigen chromatography in the eluate. There may be "process impurities" present. These are impurities that are present as a result of the process in which the protein of interest is produced. For example, these include host cell proteins (HCP), RNA, and DNA. "HCP" refers to proteins, not related to the protein of interest, produced by the host cell during cell culture or fermentation, including intracellular and/or secreted proteins. An example of a host cell protein is a protease, which can cause damage to the protein of interest if still present during and after purification. For example, if a protease remains in the sample comprising the protein of interest, it can create product-related substances or impurities which were not originally present. The presence of proteases can cause decay, e.g. fragmentation, of the protein of interest over time during the purification process, and/or in the final formulation.

In one embodiment, the host cell proteins are produced/derived from a mammalian cell or a bacterial cell. In a further embodiment the mammalian cell is selected from a human or rodent (such as a hamster or mouse) cell. In a yet further embodiment the human cell is a HEK cell, the hamster cell is a CHO cell or the mouse cell is a NS0 cell.

In certain embodiments the host cell is selected from the group consisting of selected from the group consisting of CHO cells, NS0 cells, Sp2/0 cells, COS cells, K562 cells, BHK cells, PER.C6 cells, and HEK cells (i.e., the host cell proteins are derived from these host cells). Alternatively, the host cell may be a bacterial cell selected from the group consisting of E. coli (for example, W3110, BL21), B. subtilis and/or other suitable bacteria; eukaryotic cells, such as fungal or yeast cells (e.g., Pichia pastoris, Aspergillus sp., Saccharomyces cerevisiae, Schizosaccharomyces pombe, Neurospora crassa).

The "solution" may be a cell culture medium, for example a cell culture feedstream. The feedstream may be filtered. The solution may be a Clarified Unprocessed Broth (CUB) (or clarified fermentation broth/supernatant). The CUB is also known as a cell culture supernatant with any cells and/or cellular debris removed by clarification. The solution may be a lysed preparation of cells expressing the protein (e.g. solution is a lysate).

Process impurities also include components used to grow the cells or to ensure expression of the protein of interest, for example, solvents (e.g. methanol used to culture yeast cells), antibiotics, methotrexate (MTX), media components, flocculants, etc. Also included are molecules that are part of the superantigen solid phase that leach into the sample during prior steps, for example, Protein A, Protein G, or Protein L.

Impurities also include "product-related variants" which include proteins that retain their activity but are different in their structure, and proteins that have lost their activity because of their difference in structure. These product-related variants include, for example, high molecular weight species (HMWs), low molecular weight species (LMWs), aggregated proteins, prescursors, degraded proteins, misfolded proteins, underdisulfide-bonded proteins, fragments, and deamidated species.

The presence of any one of these impurities in the eluate can be measured to establish whether the wash step has been successful. For example, we have shown a reduction in the level of HCP, expressed as ng HCP per mg product (see the Examples). Alternatively, the HCP detected can be expressed as "parts per million" or "ppm", which is equivalent to ng/mg, or "ppb" ("parts per billion"), which is equivalent to pg/mg.

In one embodiment, after step (c) the amount of HCP is less than about 200 ng HCP/mg product (i.e. ng/mg); less than about 150 ng/mg; less than about 100 ng/mg; less than about 50 ng/mg; or less than about 20 ng/mg.

A reduction may also be shown when compared to a control wash step without an aliphatic carboxylate, and/or when compared to the solution (e.g. clarified unprocessed broth) prior to purification.

In one embodiment, after step (c) the relative reduction factor of HCP—compared to a previously published 100 mM caprylate wash (e.g. see WO2014/141150)—is about 2-fold to about 50-fold. Therefore, in one embodiment, after step (c) the relative reduction factor of HCP compared to a wash buffer consisting essentially of 100 mM caprylate is about 2-fold to about 50-fold. In a further embodiment, the relative reduction factor is at least about 2-fold, 5-fold, 10-fold, 15-fold, 20-fold, 25-fold, 30-fold, 35-fold, 40-fold, 45-fold or 50-fold. For the avoidance of doubt, reference to "a wash buffer consisting essentially of 100 mM caprylate" does not exclude the presence of additional components that do not materially affect the basic characteristics of the 100 mM caprylate wash, e.g. buffering salts and/or sodium acetate.

In one embodiment, the recovery of the protein of interest from the eluate is 100%, 99%, 98%, 97%, 96%, 95%, 90%, 85%, 80%, 70%, 60%, 50% k or less, including any discrete value within the range of 100% to 50% or any sub-range defined by any pair of discrete values within this range, following the wash step of the invention. In one embodiment, the recovery of the protein of interest from the eluate is more than 70%, such as more than 75%, 80%, 85%, 90% 95% or 99%. Percent (%) recovery in the eluate is calculated by determining the amount of protein of interest in the eluate as a percentage of the amount of protein of interest applied to the column according to the following formula:

Percentage Recovery=Amount of product in the eluate÷amount of product applied to the column×100

The amount of impurities (i.e. host cell proteins) present in the eluate may be determined by ELISA, OCTET, or other methods to determine the level of one or more of the impurities described above. In the Examples described herein, an ELISA method is used to determine the level of HCP in a sample.

In one embodiment the host cell protein is selected from PLBL2 (Phospholipase B-Like 2 protein) and/or cathepsin L.

In one embodiment the host cell protein is PLBL2. Therefore, in one aspect of the invention, there is provided a method of purifying a recombinant polypeptide from phospholipase B-like 2 protein (PLBL2), the method comprising: (a) applying a solution comprising the recombinant polypeptide and PLBL2 to a superantigen chromatography solid support, (b) washing the superantigen chromatography solid support with a wash buffer comprising about 150 mM to about 850 mM caprylate; and (c) eluting the recombinant polypeptide from the superantigen chromatography solid support.

In another aspect of the invention, there is provided a method of purifying a recombinant polypeptide from phospholipase B-like 2 protein (PLBL2), the method comprising: (a) applying a solution comprising the recombinant polypeptide and PLBL2 to a superantigen chromatography solid support, (b) washing the superantigen chromatography solid support with a wash buffer comprising about 55 mM to about 850 mM caprylate and about 0.25 M to about 1.5 M arginine; and (c) eluting the recombinant polypeptide from the superantigen chromatography solid support.

In another aspect of the invention, there is provided a method of purifying a recombinant polypeptide from phospholipase B-like 2 protein (PLBL2), the method comprising: (a) applying a solution comprising the recombinant polypeptide and PLBL2 to a superantigen chromatography solid support, (b) washing the superantigen chromatography solid support with a wash buffer comprising about 100 mM caprylate and about 1.1 M arginine; and (c) eluting the recombinant polypeptide from the superantigen chromatography solid support.

PLBL2 has been found to be a HCP impurity that is difficult to remove during the downstream processing of antibodies, in particular mAb5 (see Examples), due to apparent binding to the product molecule. Therefore, in one embodiment, the recombinant polypeptide is an antibody, such as an IgG antibody, in particular an IgG4 antibody. PLBL2 amount can be measured using methods known in the art, such as by ELISA, for example the PLBL2-specific ELISA described in the Examples or disclosed in WO2015/038884.

Cathepsin L protease is produced during CHO cell culture and it can potentially degrade antibodies, such as the mAb3 product molecule (see Examples). Therefore, in one embodiment, the recombinant polypeptide is an antibody, such as an IgG antibody, in particular an IgG1 antibody.

In one embodiment the host cell protein is cathepsin L. In this embodiment, the purification of the recombinant polypeptide from cathepsin L can be measured by a reduced cathepsin L activity (for example with PromoKine PK-CA577-K142) in the eluate of step (c).

In one aspect of the invention, there is provided a method of purifying a recombinant polypeptide from cathepsin L, the method comprising: (a) applying a solution comprising the recombinant polypeptide and cathepsin L to a superantigen chromatography solid support, (b) washing the superantigen chromatography solid support with a wash buffer comprising about 150 mM to about 850 mM caprylate; and (c) eluting the recombinant polypeptide from the superantigen chromatography solid support.

In another aspect of the invention, there is provided a method of purifying a recombinant polypeptide from cathepsin L, the method comprising: (a) applying a solution comprising the recombinant polypeptide and cathepsin L to a superantigen chromatography solid support, (b) washing the superantigen chromatography solid support with a wash buffer comprising about 55 mM to about 850 mM caprylate and about 0.25 M to about 1.5 M arginine; and (c) eluting the recombinant polypeptide from the superantigen chromatography solid support.

In another aspect of the invention, there is provided a method of purifying a recombinant polypeptide from cathepsin L, the method comprising: (a) applying a solution comprising the recombinant polypeptide and cathepsin L to a superantigen chromatography solid support, (b) washing the superantigen chromatography solid support with a wash buffer comprising about 150 mM caprylate and about 1.1 M arginine; and (c) eluting the recombinant polypeptide from the superantigen chromatography solid support.

In one aspect of the invention, there is provided a purified recombinant polypeptide obtained by any one of the purification methods defined herein.

The invention will now be described with reference to the following, non-limiting examples.

Polysorbate Degradation

Polysorbates, such as polysorbate 20 and polysorbate 80 are non-ionic surfactants widely used to stabilize protein pharmaceuticals in the final formulation product. Polysorbates can be degraded by residual enzymes in the pharmaceutical product, which may impact the ultimate shelf-life of the product. Without being bound by theory, the methods described herein reduce the amount of degraded polysorbate by reducing the amount of residual host cell proteins in the final product. In one embodiment, the amount of degraded polysorbate is less than about 50%, about 40%, about 30%, about 20%, about 10%, about 5%, about 4%, about 3%, about 2%, or about 1%.

Example 1: Screening and Optimization of pH and Sodium Caprylate Concentration in Protein A Wash Introduction In the work described herein the protein A wash was optimized to achieve sufficient HCP removal with a two-column process (protein A followed by anion exchange) for all mAb products. Existing platform processes frequently require a second polishing step to achieve the required HCP level. Eliminating a chromatography step simplifies the process, enables faster process development, and could mitigate facility fit risks. The strategy for wash optimization was to improve HCP clearance by disrupting HCP-mAb interactions. Various wash additives and wash pHs were screened and then optimized for total HCP removal across the protein A process.

Materials and Methods

Sodium n-octanoate, glacial acetic acid, sodium acetate, sodium hydroxide, benzyl alcohol and trizma base were purchased from Sigma-Aldrich Chemical Co. (St. Louis, Mo.). Solutions were made using water which was further purified using a Millipore Milli-Q® system. Any pH adjustment was done using either 3 M tris base or 3 M acetic acid.

Chinese Hamster Ovary (CHO) Cell Culture for mAb Production

Clarified unfiltered broth (CUB) contained one of several GSK mAb products such as mAb1 (IgG1, pI=8.7, MW=149 kDa), mAb2 (IgG1, pI=8.3, MW=149 kDa), mAb3 (IgG1, pI=7.9, MW=149 kDa), mAb4 (IgG1, pI=8.6, MW=148 kDa), or mAb5 (IgG4, pI=7.1, MW=145 kDa). Similar methods were used to produce and harvest all mAbs used in this study. For example, mAb1 was prepared by seeding 2 liter reactors with mAb1-expressing DG44 cells at a viable cell count of 1.23-1.24 MM/mL and a viability of ~93.8%. The culture was then maintained at ~34° C., pH~6.9, and 6 g/L of glucose for 16 days. The agitation rate was maintained at ~300 rpm. Following culturing, the unclarified cell and mAb containing culture fluid was batch-centrifuged at 10,000 g for 20 minutes. The culture fluid was then vacuum-filtered through a 0.45 μM and a 0.2 μM SFCA filter from Nalgene.

Protein A Purification

MabSelect SuRe™ (MSS) protein A resin from GE Healthcare was packed in a 0.5 cm diameter column to a final bed height of 25 cm. The resin was flow-packed, after gravity settling, in 0.4 M NaCl at a linear flowrate of 475 cm/hr for 2 hours using an ÄKTA Avant 25. The packing quality was assessed with a 100 μL injection of 2M NaCl to confirm the asymmetry was 1.0+/−0.2 and at least 1000 plates per meter. All protein A experiments used a load ratio of 35 mg mAb/mL resin and all process flow rates were equivalent to a linear velocity of 300 cm/hr. The protein A chromatography method and buffers are described in Table 2.

TABLE 2

Operating Conditions for Protein A Chromatography (WO2014/141150).

| Chromatography Step: | Composition: | Volume: |
|---|---|---|
| 1. Equilibration | 55 mM Tris Base, 45 mM Acetic Acid, pH 7.5 | 3 CV |
| 2. Sample Load | Clarified unprocessed bulk (CUB), load ratio = 35 mg/mL | |
| 3. Caprylate-containing Wash: | 55 mM Tris Base, 45 mM Acetic Acid, indicated concentration of sodium caprylate, indicated pH | Varied |
| 4. Equilibration | 55 mM Tris Base, 45 mM Acetic Acid, pH 7.5 | 3 CV |
| 5. Elution | 1.8 mM Sodium Acetate, 28.2 mM Acetic Acid, pH 3.6 | 3 CV |
| 6. Strip | 300 mM Acetic Acid, pH 2.6 | 3 CV |
| 7. Neutralization | 55 mM Tris Base, 45 mM Acetic Acid, pH 7.5 | 1 CV |
| 8. Cleaning | 0.1M Sodium Hydroxide | 3 CV |
| 9. Storage | 33 mM Acetic Acid, 167 mM Sodium Acetate, 2% Benzyl Alcohol (V/V) pH 5.5 | 3 CV |

Wash Optimization

Previous studies have shown that many difficult-to-remove HCP impurities are directly associated with mAbs (Levy et al., (2014) *Biotechnol. Bioeng.* 111(5):904-912; Aboulaich et al., (2014) *Biotechnol. Prog.* 30(5):1114-1124); solution conditions that disrupt the HCP-mAb interactions are likely to provide improved HCP clearance during the protein A wash step and in this work various wash solutions were screened and optimized for this purpose. Specifically, wash solutions containing different concentrations of sodium caprylate at varying pH were used following sample load to clear HCP from the protein A-adsorbed mAb prior to elution. In order to evaluate and quantify each wash's effectiveness of HCP removal, an in-house HCP ELISA was developed as described in the ELISA methods section below. Sodium caprylate was previously found to provide robust HCP clearance when used in a protein A wash. However, previous studies were limited to sodium caprylate concentrations below 100 mM and pH 7.5; an initial scoping study was followed by a spherical central composite design study to characterize the behavior of sodium caprylate protein A washes across ranges of concentration and pH. These designs are shown in Tables 3 and 4 below. Statistical modeling was completed according to the statistical analysis methods section below.

Analysis

Protein A Yield

Protein A yield was determined by measuring mAb concentration in the eluate using a Nanodrop 2000c (Thermo Scientific). Three Nanodrop readings for each eluate sample were averaged to determine protein concentration; total mAb content in the protein A eluate was calculated by multiplying mAb concentration by eluate volume (determined from chromatogram). The mAb concentration in the load was determined using a POROS® A 20 µM Column on an Agilent 1100 series HPLC. The raw data for each CUB sample on analytical protein A was compared to a standard with known concentration for each particular mAb to calculate a titer. Total load volume was multiplied by the measured titer to calculate a total mass of mAb loaded, and yield was calculated by dividing total mAb in eluate by total mAb in the load.

Host Cell Protein (HCP) Concentration Measurement: HCP ELISA

Host cell protein analysis using HCP ELISA was developed in-house to quantify the total amount of immunogenic HCP in CHO-derived product samples (Mihara et al., (2015) J. Pharm. Sci. 104: 3991-3996). This HCP ELISA was developed using custom goat anti-CHO HCP polyclonal antibodies and an in-house produced HCP reference standard for multi-product use across CHO-derived products.

Statistical Analysis

To analyze wash performance in terms of HCP clearance and yield, a scoping experiment and central composite design study were performed. The factors were both scaled to the −1, 1 unit scale and a general linear model was fitted to the data. A separate model was fit to each response. Once the final model was selected, model assumptions on the residual were assessed and a transformation was performed as appropriate. All model terms were assessed against a 5% significance level and backwards elimination was performed, starting with the full model, including all quadratic factor terms.

MabSelect SuRe Equilibrium Isotherm Measurement

MabSelect SuRe™ resin was buffer exchanged into DI water to generate a ~50% slurry. The slurry was added to a ResiQuot, dried with a house vacuum line, and 20.8 µL resin plugs were dispensed into a 96-deep well plate. In a separate 96-well plate, protein solutions were generated between 0 and 10 mg/mL with 100, 250 and 500 mM sodium caprylate. The protein concentration was measured for each solution followed by the addition of 1 mL to each resin plug. The resin-protein mixture was equilibrated overnight with agitation. The resin was removed by filtration directly into a UV 96-well plate, and the final concentration was measured. Adsorbed protein concentration, q, was calculated with the following equation:

$$q = V_{liquid}(C_0 - C_f)/V_{resin}.$$

Results and Discussion

The results presented in this section demonstrate that a high concentration of sodium caprylate (>100 mM) removes significantly more host cell protein (HCP) during protein A chromatography than previously published sodium caprylate-based protein A wash buffers. This was demonstrated using several mAbs with relatively high HCP levels as a model and was confirmed by statistical experimental design; the CUB (protein A load) for the mAbs tested had HCP concentrations between $10^6$ and $10^7$ ng/mg.

The primary goal of this work was to assess the impact of sodium caprylate concentration and pH of the wash buffer on HCP clearance across the protein A chromatography step. The main objectives were two-fold. The first was to understand the impact on HCP across the full working range of sodium caprylate concentration and pH. A scoping design was used to explore the entire range of both parameters (Table 3); the maximum sodium caprylate concentration was 1 M, and the pH range was 7-9. The second objective was to optimize sodium caprylate concentration and pH for HCP clearance, while maintaining acceptable step yield. A spherical Central Composite Design (CCD, Table 4) was used for this optimization. Both the scoping and CCD studies used mAb1 as a model mAb. The findings from these initial studies were tested on additional mAbs. The results from both the scoping and the CCD are presented below.

TABLE 3

Scoping study design to explore sodium caprylate concentrations up to 1M and pH from 7.0 to 9.0 in the protein A wash.

| Wash number | Sodium Caprylate conc. (mM) | pH |
|---|---|---|
| 1 | 0 | 7.0 |
| 2 | 250 | 7.5 |
| 3 | 500 | 8.0 |
| 4 | 750 | 8.5 |
| 5 | 1000 | 9.0 |

TABLE 4

Spherical central composite experimental design to optimize the sodium caprylate concentration and pH in the protein A wash.

| Wash number | Sodium caprylate conc. (mM) | pH |
|---|---|---|
| 1 | 150 | 8.0 |
| 2 | 250 | 7.0 |
| 3 | 250 | 8.5 |
| 4 | 500 | 8.7 |
| 5 | 500 | 8.0 |
| 6 | 500 | 7.3 |
| 7 | 750 | 8.5 |
| 8 | 750 | 7.5 |
| 9 | 850 | 8.0 |

The results obtained from the CCD study are presented in Table 5. Overall, the pH of the protein A wash buffer had minimal impact on HCP clearance. Washes containing 500 mM or 750 mM sodium caprylate had nearly identical HCP levels across the entire pH range tested. Statistical Analysis was performed as described in the Methods Section. Briefly, separate models were fit to each response (yield and HCP), and the model terms were assessed against 5% significance using an F-test. The F-test confirmed that the wash pH did not have a statistically significant effect on HCP concentration. Similar analysis also confirmed that pH was not a significant factor for percent yield.

TABLE 5

Results of central composite design for sodium caprylate concentration and pH of protein A wash solutions (tested with mAb1).

| Sodium caprylate conc. (mM) | pH | HCP (ng/mg) | % Yield |
|---|---|---|---|
| 150 | 8.0 | 205.8 | 98.7 |
| 250 | 7.5 | 69.9 | 87.5 |
| 250 | 8.5 | 31.4 | 94.3 |
| 500 | 7.3 | 17.1 | 77.4 |
| 500 | 8.0 | 18.2 | 75.7 |
| 500 | 8.7 | 19.0 | 76.0 |
| 750 | 7.5 | 17.2 | 73.7 |
| 750 | 8.5 | 13.6 | 74.1 |
| 850 | 8.0 | 15.5 | 70.1 |

Statistical analysis of CCD results confirmed that sodium caprylate concentration is a significant factor—with both linear and quadratic terms—for both HCP clearance and percent yield. HCP concentration (ng/mg) was reduced by two orders of magnitude when sodium caprylate concentration was increased from 0 to 1 M (FIG. 1—Percent yield (triangles, ▲) and HCP concentration (squares, ■)). However, as sodium caprylate concentration increases beyond 250 mM, yield drops from above 90% to 70% (FIG. 1). This large decrease in step yield above 250 mM sodium caprylate could be due to the formation of caprylate micelles. The caprylate critical micelle concentration (CMC) in the protein A wash buffer was experimentally determined to be 340 mM. When the concentration of sodium caprylate was increased from 250 mM to 500 mM there was a 15% decrease in yield and only a 2.8% decrease in HCP. This may indicate that the free form of sodium caprylate is the active form for HCP removal, while any concentration above the CMC shows diminishing returns because the caprylate micelles cause yield loss.

Example 2: Investigation of Yield Loss and Potential Mitigation Strategies

Figure 2:
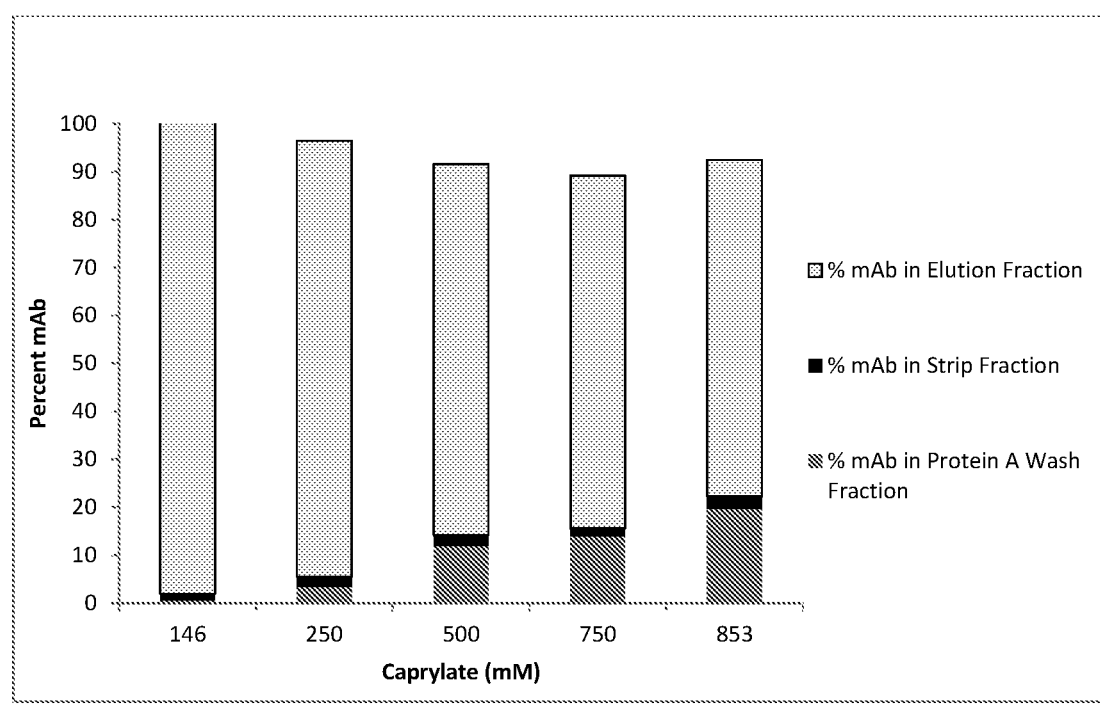
FIG. 2: Percent of loaded mAb1 in elution, strip, and wash fractions for 5 concentrations of sodium caprylate in the wash buffer.

The decrease in percent yield above the CMC suggests that caprylate micelles—rather than the free form of caprylate—could reduce yield across the protein A step. To determine the nature of the yield loss, mAb concentration was measured in the eluate, strip, and wash fractions for protein A processes with varying sodium caprylate washes (FIG. 2). This result demonstrates that the yield loss at high sodium caprylate concentration was due to desorption during the wash step.

Figure 3:
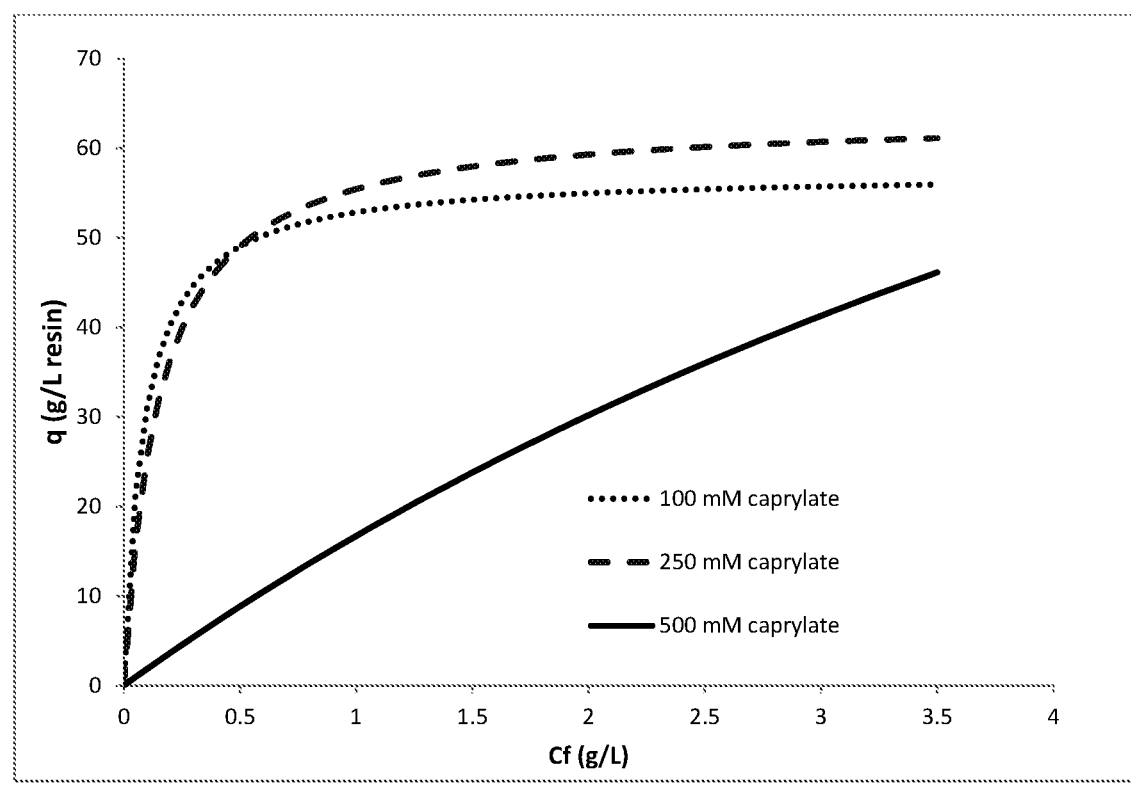
FIG. 3: Langmuir isotherm fits for mAb1 adsorption the MabSelect SuRe resin in solutions of different sodium caprylate concentration.

To further characterize the yield loss during high sodium caprylate washes, equilibrium binding isotherms were measured to determine the mAb capacity loss at high sodium caprylate concentrations (FIG. 3). The previously published caprylate wash—containing 100 mM sodium caprylate—had a maximum binding capacity of 57 g/L when fit with the Langmuir isotherm. The adsorption isotherm was similar at 250 mM sodium caprylate, but at 500 mM sodium caprylate the Langmuir isotherm was a poor fit. This result confirms that high concentration sodium caprylate washes decrease the binding capacity of the protein A resin and cause a yield loss.

After determining the source of yield loss, methods for reducing yield loss were investigated. The two strategies that were investigated were decreased wash volume and decreased load ratio. The 250 mM sodium caprylate wash was tested at 4, 6, and 8 CVs. Decreasing the wash length from 8 to 4 CVs only provided a 2% increase in yield (Table 6), and the HCP concentration only increased from 31.0 to 35.8 ng/mg. This indicated that high sodium caprylate washes can achieve acceptable HCP levels with smaller volumes than tested during initial scoping and CCD studies, and it also demonstrated that smaller wash volumes do not compensate for decreased binding capacity with high sodium caprylate concentrations.

TABLE 6

HCP concentration and protein A step yield for different volumes of a 250 mM sodium caprylate wash using mAb1 as a model.

| Wash volume (CV) | HCP (ng/mg) | % Yield |
| --- | --- | --- |
| 4 | 35.8 | 89.7 |
| 6 | 33.0 | 89.6 |
| 8 | 31.0 | 87.7 |

Decreased load ratio during protein A capture was also investigated as a mitigation for yield loss during high concentration sodium caprylate washes (Table 7). When the load ratio was decreased from 30 mg/ml to 10 mg/ml, yield increased by 4.7% and 7.7% for 250 mM and 500 mM sodium caprylate washes, respectively. Load ratio had minimal impact on HCP concentration in the protein A eluate.

TABLE 7

HCP concentration and protein A step yield for varying protein A load ratios with both 250 mM and 500 mM sodium caprylate washes using mAb1 as a model.

| Sodium caprylate conc. (mM) | Load ratio (g/L) | HCP (ng/mg) | % Yield |
| --- | --- | --- | --- |
| 250 | 10 | 42.3 | 95 |
| 250 | 15 | 38.1 | 92.8 |
| 250 | 20 | 46.3 | 92.3 |
| 250 | 25 | 41.9 | 91.8 |
| 250 | 30 | 40.2 | 90.2 |
| 500 | 10 | 24.5 | 88.5 |
| 500 | 15 | 23.4 | 86.9 |
| 500 | 20 | 20.2 | 85.5 |
| 500 | 25 | 18.6 | 84.8 |
| 500 | 30 | 16.9 | 80.8 |

Example 3: Performance of Improved Wash with Additional mAbs

Figure 4:
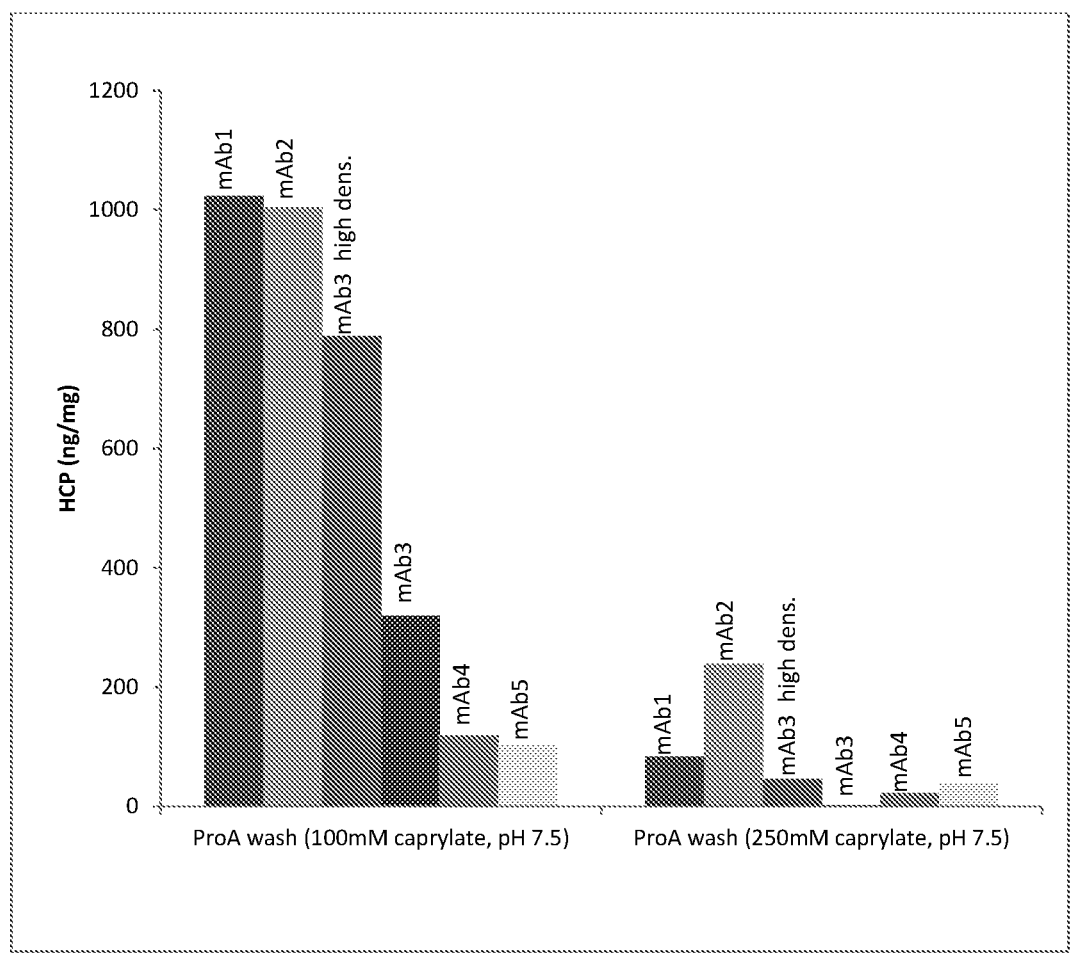
FIG. 4: Protein A eluate HCP concentration for 5 mAbs with 100 mM and 250 mM sodium caprylate wash buffers.

The preceding protein A wash optimization studies were completed using only mAb1 as the model product. The CCD study confirmed that pH was not a significant factor for HCP removal. The statistical analysis and subsequent yield investigations indicated that sodium caprylate concentration was optimal up to 400 mM. To confirm the improved HCP removal of the 250 mM sodium caprylate wash over the previously developed 100 mM sodium caprylate wash, additional mAbs were studied in this section. The HCP concentration in the protein A eluate for 5 mAbs was compared for washes containing either 100 or 250 mM sodium caprylate (FIG. 4). One mAb (mAb3) was sourced from two separate upstream processes: a high-cell density process with higher levels of HCP and a standard process that is comparable to the other molecules studied.

With the exception of mAb2, all mAbs tested here had less than 100 ng/mg in the protein A eluate when using the 250 mM sodium caprylate wash. In most cases, the HCP concentration was improved by approximately an order of magnitude simply by increasing sodium caprylate concentration in the wash. Additionally, these mAbs had acceptable step yield and product quality with the elevated sodium caprylate concentration.

Example 4: Addition of Arginine to Sodium Caprylate-Based Protein a Washes

Arginine—an amino acid—has very different physical and chemical properties compared to sodium caprylate, a fatty acid. It was hypothesized that the structural differences between these two additives could lead to orthogonal HCP removal mechanisms, i.e. mixtures of arginine and caprylate could have better HCP removal than a wash containing only a single component. The following studies were completed to assess both the total HCP removal and specific HCP removal for caprylate/arginine mixtures.

Total HCP Clearance with Caprylate/Arginine Protein a Wash Buffer

Protein A wash buffers containing combinations of sodium caprylate and arginine were tested with mAb1 and mAb2. The results for mAb2 are presented in FIG. 5. Protein A wash buffers containing only 100 mM sodium caprylate or 750 mM arginine resulted in HCP concentrations between 700 and 1300 ng/mg. Increasing the sodium caprylate concentration to 250 mM resulted in a large improvement for HCP clearance—consistent with 'high sodium caprylate' results discussed hereinbefore. A wash containing 250 mM sodium caprylate at pH 8.5 resulted in 273 ng/mg HCP in the protein A eluate. The addition of arginine to the caprylate-based protein A wash further improved the HCP removal: 250 mM sodium caprylate with 750 mM arginine at either pH 7.5 or 8.5 resulted in HCP concentrations of 209 and 144 ng/mg, respectively.

Figure 6:
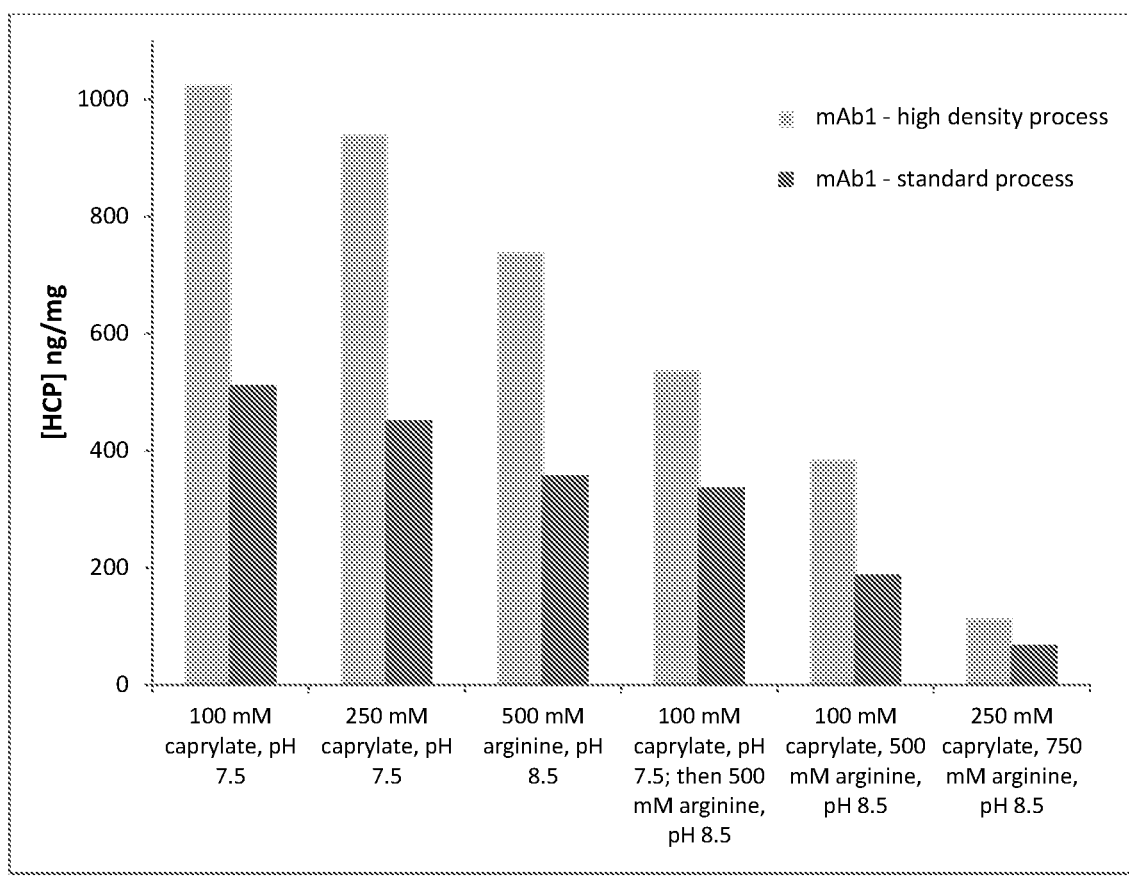
FIG. 6: Protein A eluate HCP concentration for two different mAb1 feed streams with wash buffers containing different concentrations of sodium caprylate and arginine at varying pH. Note: all wash buffers contain 300 mM sodium acetate.

A similar caprylate/arginine study was completed with mAb1. mAb1 was sourced from two separate upstream processes: a 'standard' fed-batch bioreactor and high cell density process. The high cell density process resulted in higher product titers and HCP concentration. It was included in this study as a 'worst case' feed material. The results are presented in FIG. 6.

Figure 5:
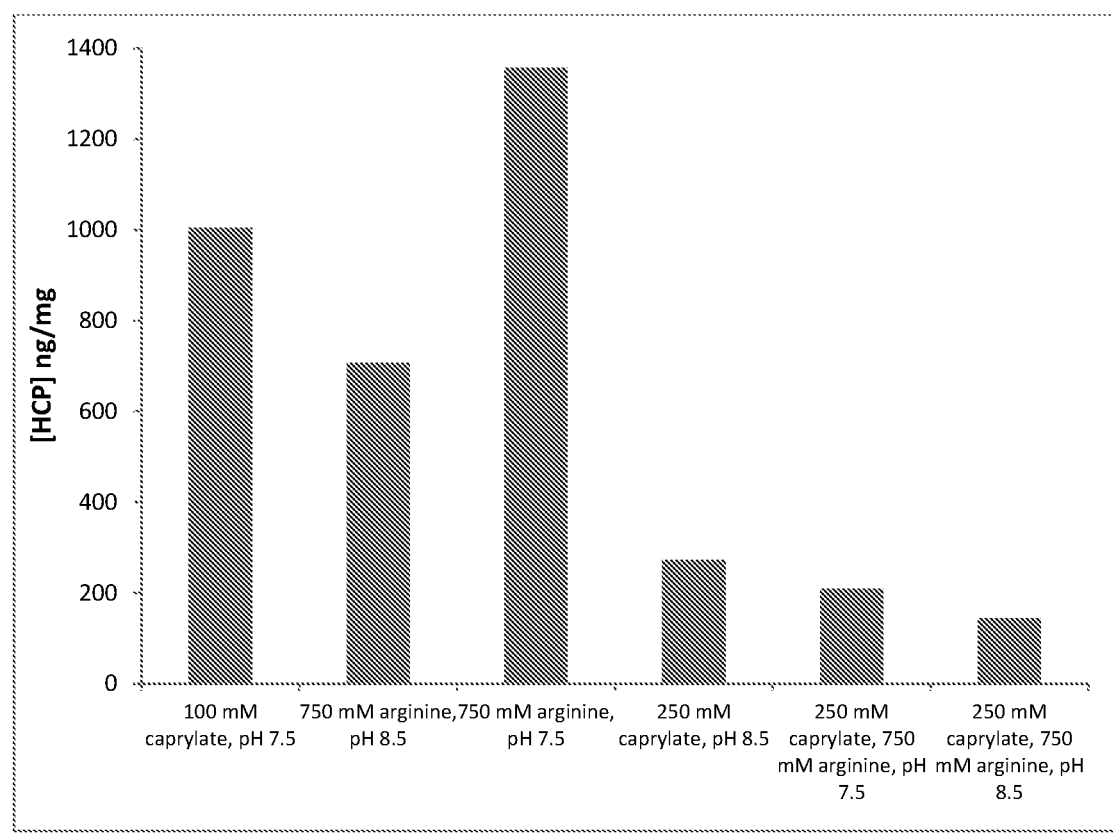
FIG. 5: Protein A eluate HCP concentration for mAb2 with wash buffers containing different concentrations of sodium caprylate and arginine at varying pH. Note: all wash buffers contain 300 mM sodium acetate.

Overall, the mAb1 results are similar to the mAb2 findings presented in FIG. 5. For both the standard mAb1 feed stream and the high density material, there was improved HCP clearance by increasing sodium caprylate from 100 to 250 mM. Additionally, 500 mM arginine had better HCP clearance than either sodium caprylate-only wash. However, washing with both sodium caprylate and arginine—either as a mixture or by applying sequential washes—showed improved HCP clearance over either component individually. The best performance was a wash containing 250 mM sodium caprylate and 750 mM arginine at pH 8.5. This combination of high sodium caprylate and arginine produced protein A eluates of 113 and 67 ng/mg for high density and standard mAb1, respectively.

Example 5: Caprylate/Arginine Protein a Wash to Remove PLBL2

PLBL2 is a specific HCP impurity that is difficult to remove during the downstream processing of mAb5, an IgG4, due to apparent binding to the product molecule. This particular HCP impurity has previously been found to bind to IgG4 products during downstream processing. PLBL2 also causes 'dilutional non-linearity' during HCP ELISA analysis. Protein A washes containing high sodium caprylate concentration and/or arginine were tested for PLBL2 removal during the protein A step for mAb5.

Figure 7:
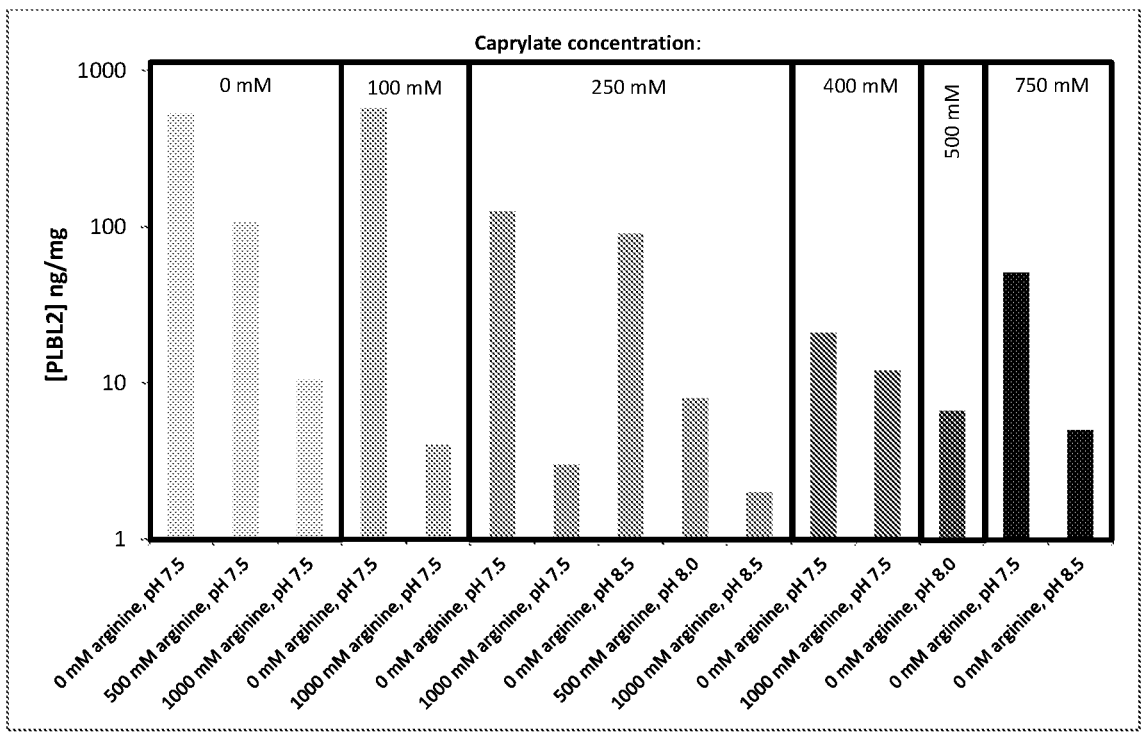
FIG. 7: Protein A eluate PLBL2 concentration for mAb5 feed streams with wash buffers containing different concentrations of sodium caprylate and arginine at varying pH.
Figure 8:
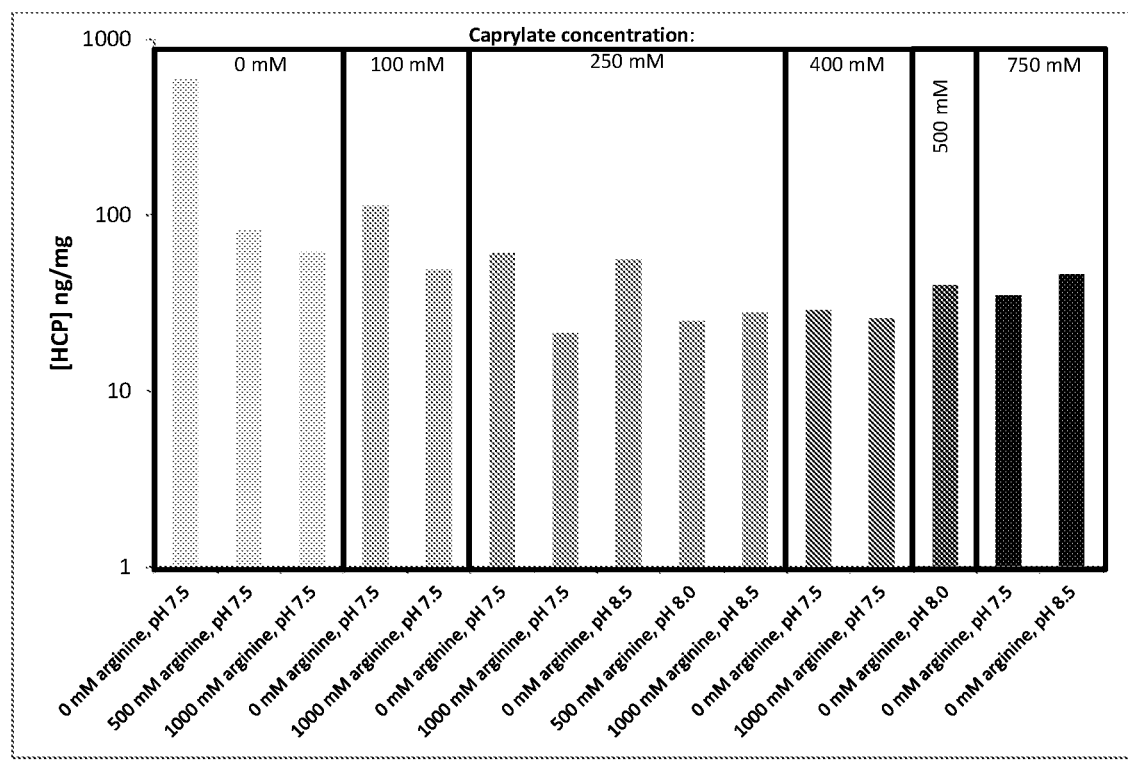
FIG. 8: Protein A eluate HCP concentration for mAb5 feed streams with wash buffers containing different concentrations of sodium caprylate and arginine at varying pH.
Figure 9:
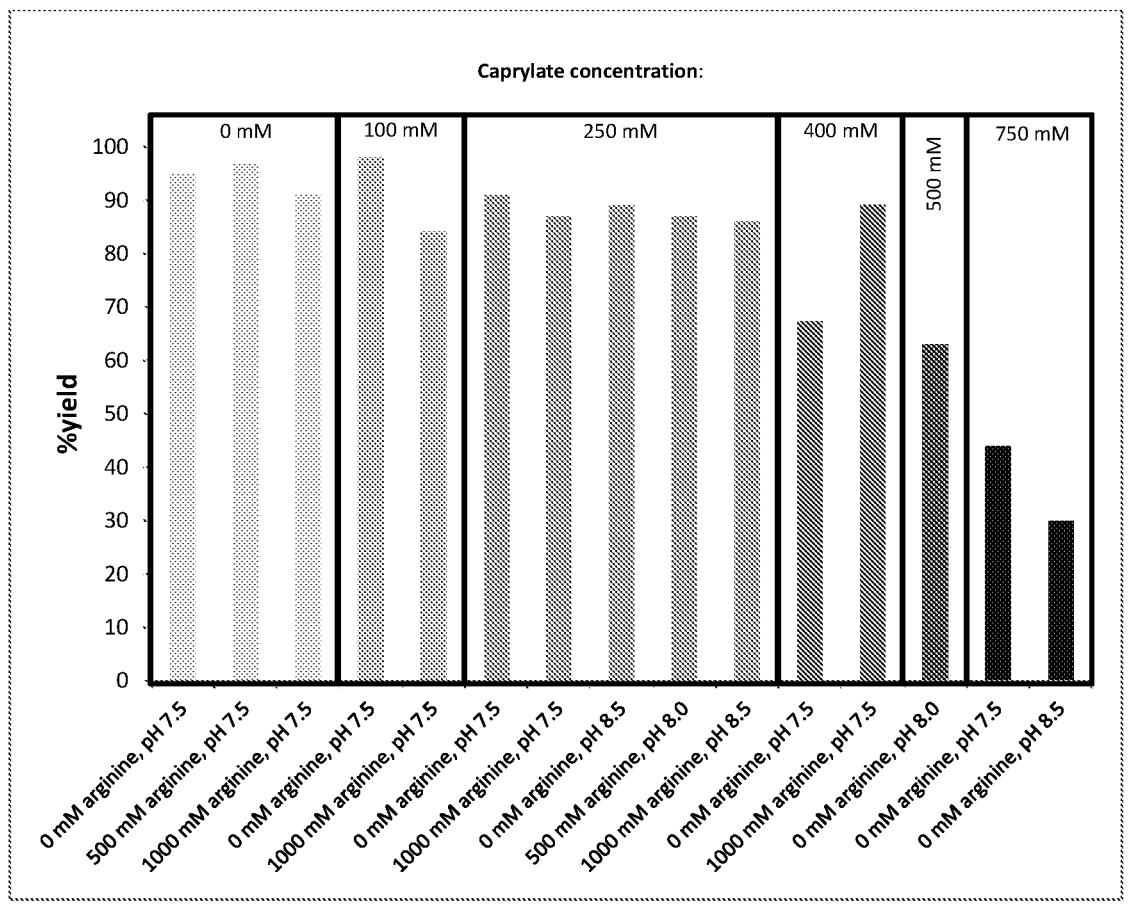
FIG. 9: Protein A step yields for mAb5 feed streams with wash buffers containing different concentrations of sodium caprylate and arginine at varying pH.

Washes were tested with sodium caprylate concentrations up to 750 mM, pH from 7.5 and 8.5, and arginine concentration up to 1 M. For each protein A wash trial the total PLBL2 concentration (FIG. 7, measured using a PLBL2-specific ELISA) was reported along with total HCP (FIG. 8), and step yield (FIG. 9).

PLBL2 concentration varied from nearly 1 to 600 ng/mg for different test washes. Washes containing no arginine and less than 100 mM sodium caprylate performed the worst and produced protein A eluate with approximately 600 ng/mg PLBL2. Increasing sodium caprylate concentration to 250 mM reduced PLBL2 to ~100 ng/mg; sodium caprylate concentrations greater than 250 mM continued to decrease PLBL2 to ~50 ng/mg, but also resulted in a yield loss. Total HCP also generally decreased with increasing sodium caprylate.

Protein A washes containing arginine were the most successful in terms of PLBL2 clearance, and they also demonstrated good removal of total HCP. 1000 mM arginine with no sodium caprylate resulted in ~10 ng/mg PLBL2 and 62 ng/mg HCP. High concentration of arginine did not cause significant yield losses.

The combination of sodium caprylate and arginine was the most effective wash for mAb5. Specifically, 250 mM sodium caprylate with 1 M arginine at pH 7.5 or 8.5 resulted in 2-3 ng/mg PLBL2 and ~20-30 ng/mg HCP while maintaining ~90% step yield. Washes containing 1 M arginine and 100 mM sodium caprylate were also successful, but resulted in slightly higher PLBL2 and HCP concentrations.

Example 6: Caprylate/Arginine Wash for Cathepsin L Activity Reduction

Protein A washes containing sodium caprylate and arginine were tested with mAb3 for cathepsin L clearance capability. Cathepsin L protease is produced during CHO cell culture and it can potentially degrade the mAb3 product molecule. It has been demonstrated that cathepsin L is not removed from mAb3 during the protein A process. Washes containing 100 mM sodium caprylate, 250 mM sodium caprylate, 100 mM sodium caprylate with 1000 mM arginine, and 100 mM sodium caprylate with 750 mM lysine were tested.

Washes containing 250 mM sodium caprylate for this specific product resulted in unexpected protein A elution behavior: the low pH elution—normally completed in ~2 column volumes—was extended over 10 column volumes. Additionally, the mAb3 protein A eluate had very high aggregate (measured by SEC) when the 250 mM sodium caprylate wash was tested. This behavior was not observed with any other products tested with high sodium caprylate washes.

Figure 10:
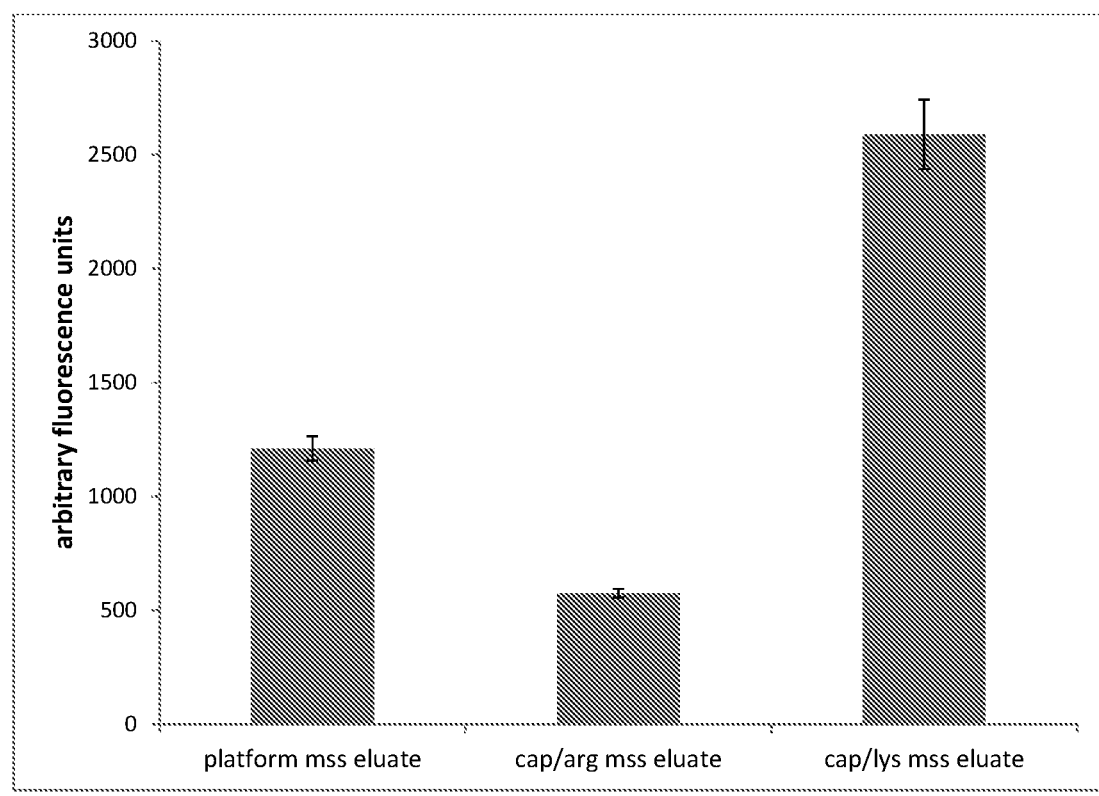
FIG. 10: Cathepsin L activities in mAb3 protein A eluates for washes containing sodium caprylate and arginine or lysine.

Protein A washes containing arginine or lysine did not have the extended elution behavior that was observed with the 250 mM sodium caprylate alone. Cathepsin L activities measured in the protein A eluates for three different washes (100 mM caprylate ("platform msss eluate"); 250 mM caprylate, 1M arginine ("cap/arg msss eluate"); 250 mM caprylate, 750 mM lysine ("cap/lys msss eluate")) are reported in FIG. 10; the protein A elution volumes are listed in Table 8. The measured activity was significantly decreased with the 100 mM sodium caprylate, 1000 mM arginine wash, and a subsequent stability study demonstrated that fragmentation was decreased for material prepared using this wash compared with the 100 mM sodium caprylate wash. The addition of 750 mM lysine, rather than arginine, successfully decreased the large elution volume, but did not significantly decrease cathepsin L activity. The combination of sodium caprylate and 1000 mM arginine provides improved cathepsin L and total HCP clearance while maintaining a reasonable elution volume and acceptable product quality attributes.

TABLE 8

Protein A eluate volume for mAb3 with different wash solutions.

| Wash | Elution volume (CVs) |
| --- | --- |
| 100 mM sodium caprylate | 1.73 |
| 250 mM sodium caprylate | 9.89 |
| 250 mM sodium caprylate, strip used for elution | 5.41 |
| 250 mM sodium caprylate, 90 mM arginine | 3.95 |

TABLE 8-continued

Protein A eluate volume for mAb3 with different wash solutions.

| Wash | Elution volume (CVs) |
|---|---|
| 250 mM sodium caprylate, then 90 mM arginine | 9.75 |
| 250 mM sodium caprylate, 750 mM lysine | 1.95 |
| 250 mM sodium caprylate, 1M arginine | 1.59 |
| 100 mM sodium caprylate, 1M arginine | 1.49 |

Example 7: Caprylate/Arginine Protein a Wash to Remove HCP

Protein A washes containing sodium caprylate and arginine were tested with mAb3 for HCP clearance capability. The wash buffer concentrations and resulting HCP concentrations are outlined in Table 9 below. The arginine/caprylate wash was compared to caprylate-only washes for mAb3.

The 150 mM caprylate wash provides significantly higher HCP clearance than the 100 mM caprylate wash. The combination of 1.1 M arginine and 150 mM caprylate further improves HCP clearance by a significant factor. The improved clearance of HCP during the protein A step enabled the removal of the final polishing chromatography step that was required in the caprylate-only process.

TABLE 9

| Caprylate (mM) | Arginine (M) | HCP (ng/mg) |
|---|---|---|
| 150 | 1.1 | 97.3 |
| 150 | 0 | 556.0 |
| 100 | 0 | 907.0 |

Example 8: Decrease in mAb3 Fragmentation

Protein A purification of mAb3 with washes containing sodium caprylate and arginine were tested for antibody fragmentation during purification. Data (FIGS. 11-13) was generated including 3 batches of wash buffer containing 100 mM caprylate wash, and 2 batches of wash buffer containing 150 M caprylate plus 1.1 M arginine.

Figure 11:
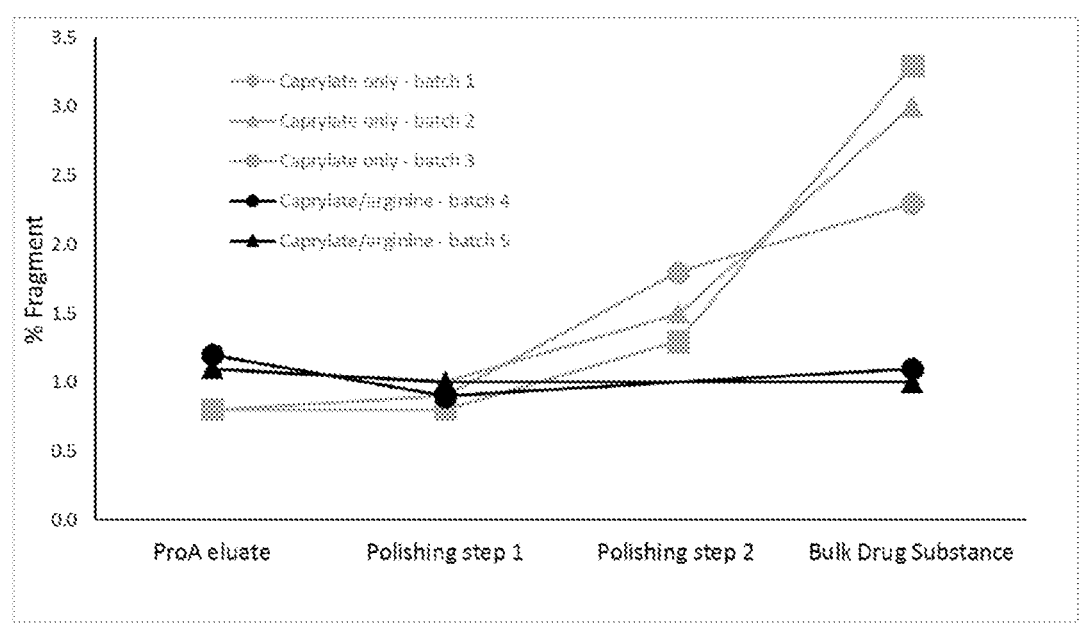
FIG. 11: Percent antibody fragmentation for monoclonal antibody process intermediates.
Figure 12:
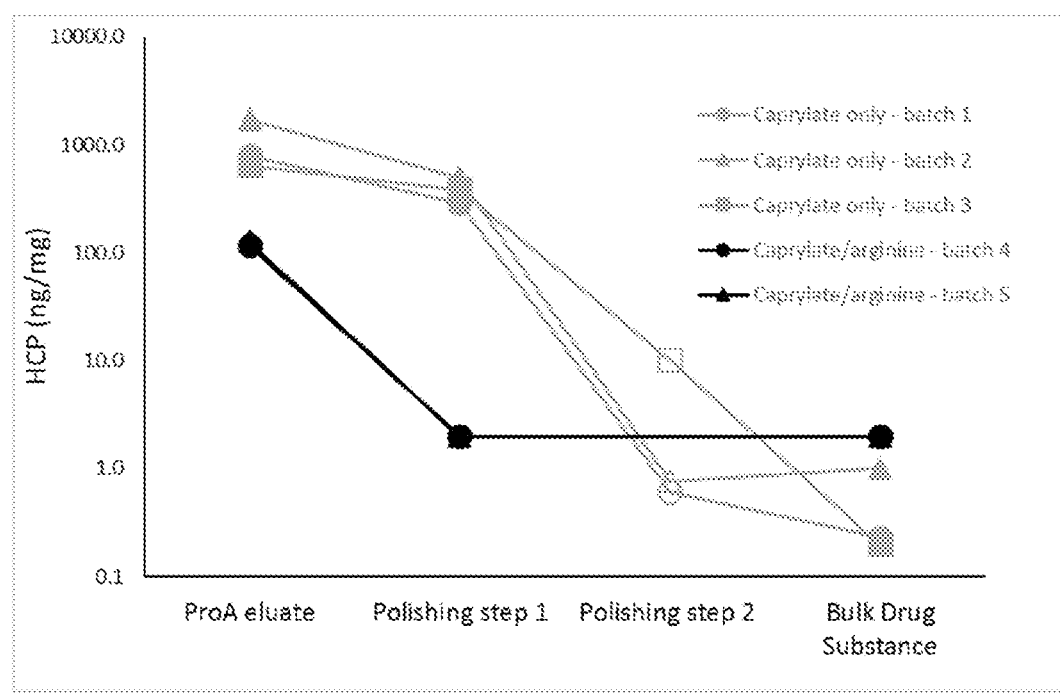
FIG. 12: HCP concentration with caprylate only versus caprylate plus arginine wash buffers.

FIG. 11 shows percent antibody fragmentation (measured with SEC HPLC) throughout the entire downstream process. FIG. 12 demonstrates HCP concentration through the process. The caprylate/arginine batches have no significant antibody fragmentation formation during the process, whereas the caprylate-only batches have significant antibody fragmentation generation after the third polishing step (not required with caprylate/arginine wash).

Figure 13:
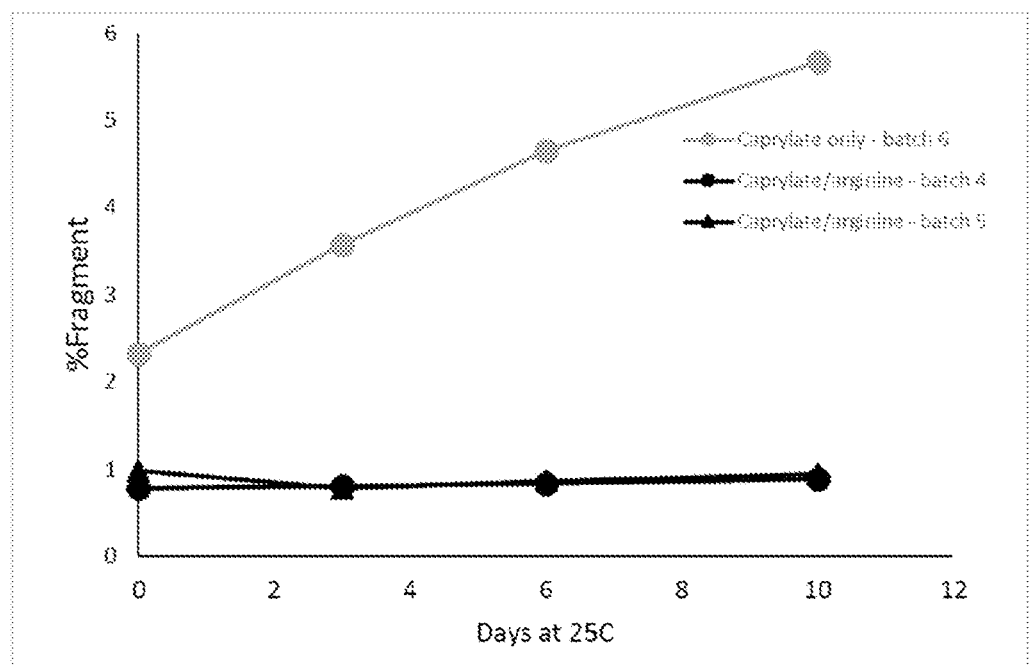
FIG. 13: Percent antibody fragmentation for monoclonal antibody bulk drug substance held at 25 C for up to 10 days.

In addition, the stability of Bulk Drug Substance produced by both processes (caprylate-only and caprylate+arginine) was compared. Bulk drug substance from the caprylate+arginine process did not generate antibody fragmentation within 10 days at 25 degrees Celsius; bulk drug substance from the caprylate-only process generates significant antibody fragmentation during the 10 days at 25 degrees Celsius (FIG. 13).

The combination of caprylate and arginine in the wash buffer significantly decreases the generation of antibody fragmentation throughout the downstream process due to improved clearance of Cathepsin L.

CONCLUSIONS

The HCP clearance across the protein A step was optimized by modifying the wash buffer to minimize HCP-mAb interactions. Initial screening studies concluded that pH of the protein A wash buffer—varied from 7 to 9—does not significantly impact HCP clearance or step yield. Sodium caprylate concentration has a strong effect on both step yield and HCP removal. At very high sodium caprylate concentrations (above the CMC) the HCP clearance is optimal, but step yield is very low. This study found that utilizing a protein A wash containing 250 mM sodium caprylate offers a large improvement of HCP clearance compared to previously used 100 mM sodium caprylate washes, while maintaining an acceptable step yield. This study also found that protein A washes containing a combination of 250 mM sodium caprylate and 500-1000 mM arginine have greater HCP clearance compared to washes containing only sodium caprylate. Protein A washes containing sodium caprylate and arginine were found to successfully remove cathepsin L and PLBL2—two particularly difficult HCP impurities—from mAb3 and mAb5, respectively.

It will be understood that the embodiments described herein may be applied to all aspects of the invention. Furthermore, all publications, including but not limited to patents and patent applications, cited in this specification are herein incorporated by reference as though fully set forth.

The invention claimed is:

1. A method of purifying a recombinant polypeptide from Host Cell Proteins (HCP), the method comprising: (a) applying a solution comprising the recombinant polypeptide and HCP to a superantigen chromatography solid support, (b) washing the superantigen chromatography solid support with a wash buffer comprising at least about 75 mM caprylate and greater than about 0.5 M arginine; and (c) eluting the recombinant polypeptide from the superantigen chromatography solid support.

2. The method according to claim 1, wherein the caprylate is sodium caprylate.

3. The method according to claim 1, wherein the wash buffer comprises about 75 mM to about 300 mM caprylate.

4. The method according to claim 1, wherein the wash buffer comprises about 0.75 M to about 1.5 M arginine.

5. The method according to claim 1, wherein the eluted recombinant polypeptide contains less than about 2% fragmented recombinant polypeptide.

6. The method according to claim 1, wherein the HCP is derived from a mammalian cell.

7. The method according to claim 1, wherein the HCP is phospholipase B-Like 2 protein.

8. The method according to claim 1, wherein the HCP is cathepsin L.

9. The method according to claim 8, wherein the purification of the recombinant polypeptide from cathepsin L is measured by a reduced cathepsin L activity in the eluate of step (c).

10. The method according to claim 1, wherein the pH of the wash buffer is between pH 7 to pH 9.

11. The method according to claim 1, wherein the recombinant polypeptide is a monoclonal antibody (mAb).

12. The method according to claim 11, wherein the mAb is an IgG1, or an IgG4.

13. The method according to claim 1, wherein the wash buffer does not contain sodium chloride.

14. The method according to claim 1, wherein the superantigen is selected from the group consisting of Protein A, Protein G, and Protein L.

15. The method according to claim 1, wherein after step (c) the amount of HCP is less than about 200 ng HCP/mg product.

16. A method of purifying a recombinant polypeptide from phospholipase B-Like 2 protein, the method comprising: (a) applying a solution comprising the recombinant polypeptide and phospholipase B-Like 2 protein to a superantigen chromatography solid support, (b) washing the superantigen chromatography solid support with a wash buffer comprising about 100 mM caprylate and about 1.1 M arginine; and (c) eluting the recombinant polypeptide from the superantigen chromatography solid support.

17. A method of purifying a recombinant polypeptide from cathepsin L, the method comprising: (a) applying a solution comprising the recombinant polypeptide and cathepsin L to a superantigen chromatography solid support, (b) washing the superantigen chromatography solid support with a wash buffer comprising about 150 mM caprylate and about 1.1 M arginine; and (c) eluting the recombinant polypeptide from the superantigen chromatography solid support.

* * * * *